United States Patent
Gregorich

(10) Patent No.: US 7,635,384 B2
(45) Date of Patent: Dec. 22, 2009

(54) VARYING CIRCUMFERENTIAL SPANNED CONNECTORS IN A STENT

(75) Inventor: Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 97 days.

(21) Appl. No.: 11/349,419

(22) Filed: Feb. 6, 2006

(65) Prior Publication Data

US 2006/0129230 A1 Jun. 15, 2006

Related U.S. Application Data

(62) Division of application No. 10/606,168, filed on Jun. 25, 2003, now Pat. No. 7,131,993.

(51) Int. Cl.
*A61F 2/06* (2006.01)
(52) U.S. Cl. .................................... 623/1.15
(58) Field of Classification Search ....... 623/1.15–1.17, 623/1.22
See application file for complete search history.

(56) References Cited

U.S. PATENT DOCUMENTS

| | | | | |
|---|---|---|---|---|
| 5,091,205 A | 2/1992 | Fan | | 427/2 |
| 5,370,683 A | 12/1994 | Fontaine | | 623/1 |
| 5,591,230 A | 1/1997 | Horn et al. | | 623/1 |
| 5,593,442 A | 1/1997 | Klein | | 623/12 |
| 5,674,241 A | 10/1997 | Bley et al. | | 606/198 |
| 5,683,450 A | 11/1997 | Goicoechea et al. | | 623/1 |
| 5,697,971 A | 12/1997 | Fischell et al. | | 623/1 |
| 5,700,285 A | 12/1997 | Meyers et al. | | 623/1 |
| 5,735,892 A | 4/1998 | Meyers et al. | | 623/1 |
| 5,749,880 A | 5/1998 | Banas et al. | | 606/198 |
| 5,755,770 A | 5/1998 | Ravenscroft | | 623/1 |
| 5,755,781 A | 5/1998 | Jayaraman | | 623/1 |
| 5,807,404 A | 9/1998 | Richter | | 623/1 |
| 5,824,046 A | 10/1998 | Smith et al. | | 623/1 |
| 5,843,117 A | 12/1998 | Alt et al. | | 606/194 |
| 5,843,158 A | 12/1998 | Lenker et al. | | 623/1 |
| 5,868,782 A | 2/1999 | Frantzen | | 606/198 |
| 5,897,589 A | 4/1999 | Cottenceau | | 623/1 |
| 5,911,754 A | 6/1999 | Kanesaka et al. | | 623/1 |

(Continued)

FOREIGN PATENT DOCUMENTS

EP 679372 11/1995

(Continued)

OTHER PUBLICATIONS

"The Jostent Coronary Stent Range," Nicolaus Reifart, "Handbook of Coronary Stents," 2002, pp. 122-125; figure 16.1.

*Primary Examiner*—Bruce E Snow
(74) *Attorney, Agent, or Firm*—Vidas, Arrett & Steinkraus, P.A.

(57) ABSTRACT

A stent comprises a plurality of serpentine circumferential bands and a plurality of connector columns. Each connector column is located between two adjacent serpentine circumferential bands and comprises a plurality connector struts. Each connector strut is connected at one end to one serpentine circumferential band and at another end to another serpentine circumferential band. Each connector column may contain multiple types of connector struts having varying circumferential spans. Each serpentine circumferential band may have sections which vary in amplitude and/or wavelength.

15 Claims, 15 Drawing Sheets

U.S. PATENT DOCUMENTS

Figure 1:
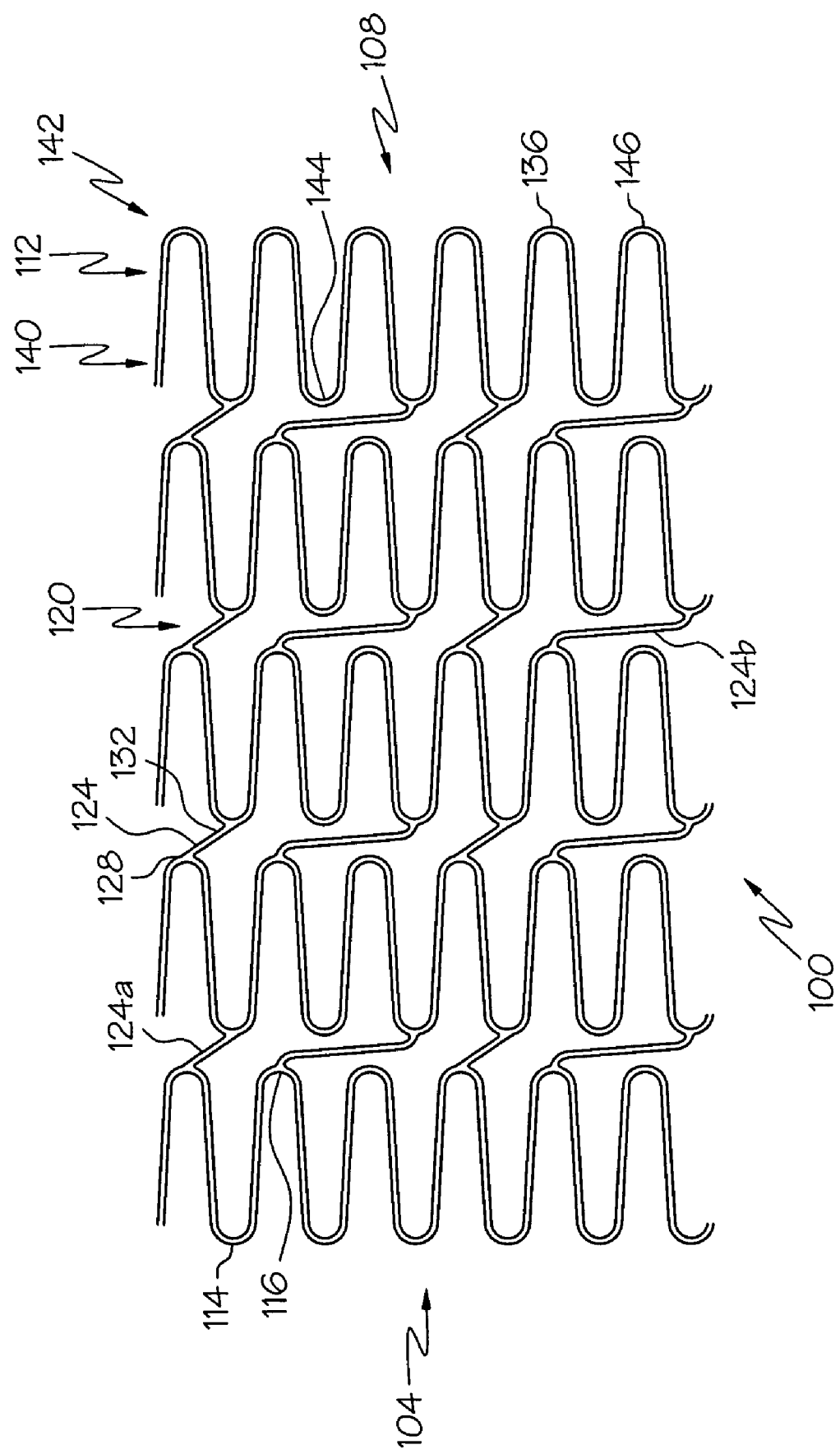

| | | | |
|---|---|---|---|
| 5,913,895 A | 6/1999 | Burpee et al. ................... 623/1 |
| 5,913,897 A | 6/1999 | Corso, Jr. et al. ................ 623/1 |
| 5,928,279 A | 7/1999 | Shannon et al. ................. 623/1 |
| 5,935,162 A | 8/1999 | Dang .............................. 623/1 |
| 5,948,016 A | 9/1999 | Jang ................................ 623/1 |
| 5,957,930 A | 9/1999 | Vrba ........................... 606/108 |
| 5,961,545 A | 10/1999 | Lentz .............................. 623/1 |
| 5,964,798 A | 10/1999 | Imran .............................. 623/1 |
| 5,980,553 A | 11/1999 | Gray et al. ................... 606/198 |
| 6,001,125 A | 12/1999 | Golds et al. ..................... 623/1 |
| 6,017,363 A | 1/2000 | Hojeibane ....................... 623/1 |
| 6,017,365 A | 1/2000 | Von Oepen ..................... 623/1 |
| 6,033,433 A | 3/2000 | Ehr et al. ......................... 623/1 |
| 6,042,597 A | 3/2000 | Kveen et al. ................. 606/198 |
| 6,068,656 A | 5/2000 | Von Oepen ................. 623/1.17 |
| 6,083,259 A | 7/2000 | Frantzen ..................... 623/1.15 |
| 6,106,548 A | 8/2000 | Roubin et al. .............. 623/1.15 |
| 6,113,627 A | 9/2000 | Jang ................................ 623/1 |
| 6,117,165 A | 9/2000 | Becker ........................... 623/1 |
| 6,120,522 A | 9/2000 | Vrba et al. .................. 606/190 |
| 6,123,712 A | 9/2000 | Di Caprio et al. .......... 606/108 |
| 6,123,721 A | 9/2000 | Jang ................................ 623/1 |
| 6,124,523 A | 9/2000 | Banas et al. .................. 623/11 |
| 6,132,460 A | 10/2000 | Thompson ..................... 623/1 |
| 6,132,461 A | 10/2000 | Thompson ................. 623/1.15 |
| 6,139,573 A | 10/2000 | Sogard et al. .............. 623/1.13 |
| 6,159,237 A | 12/2000 | Alt et al. .................... 623/1.15 |
| 6,162,243 A | 12/2000 | Gray et al. .................. 623/1.11 |
| 6,190,403 B1 | 2/2001 | Fischell et al. .................. 623/1 |
| 6,193,744 B1 | 2/2001 | Ehr et al. ......................... 623/1 |
| 6,200,334 B1 | 3/2001 | Jang ............................. 623/1.1 |
| 6,206,911 B1 | 3/2001 | Milo ........................... 623/1.15 |
| 6,217,608 B1 | 4/2001 | Penn et al. .................. 623/1.16 |
| 6,231,598 B1 | 5/2001 | Berry et al. ................. 623/1.15 |
| 6,235,053 B1 | 5/2001 | Jang ............................ 623/1.15 |
| 6,238,430 B1 | 5/2001 | Klumb et al. ............... 623/1.11 |
| 6,241,039 B1 | 6/2001 | Jarnstrom et al. ........ 180/69.21 |
| 6,273,910 B1 | 8/2001 | Limon ........................ 623/1.15 |
| 6,331,189 B1 | 12/2001 | Wolinsky et al. ........... 623/1.15 |
| 6,340,366 B2 | 1/2002 | Wijay .......................... 623/1.13 |
| 6,342,067 B1 | 1/2002 | Mathis et al. ............... 623/1.15 |
| 6,355,059 B1 | 3/2002 | Richter et al. .............. 623/1.17 |
| 6,355,063 B1 | 3/2002 | Calcote ....................... 623/1.42 |
| 6,358,274 B1 | 3/2002 | Thompson .................. 623/1.15 |
| 6,361,759 B1 | 3/2002 | Frayne et al. ............. 424/9.323 |
| 6,364,903 B2 | 4/2002 | Tseng et al. ................ 623/1.15 |
| 6,383,214 B1 | 5/2002 | Banas et al. ................ 623/1.14 |
| 6,395,212 B1 | 5/2002 | Solem ......................... 264/230 |
| 6,398,803 B1 | 6/2002 | Layne et al. ................ 623/1.13 |
| 6,409,761 B1 | 6/2002 | Jang .......................... 623/6.12 |
| 6,416,538 B1 | 7/2002 | Ley et al. .................... 623/1.15 |
| 6,451,047 B2 | 9/2002 | McCrea et al. ............. 623/1.13 |
| 6,461,380 B1 * | 10/2002 | Cox ........................... 623/1.17 |
| 6,464,720 B2 | 10/2002 | Boatman et al. ............ 623/1.15 |
| 6,475,235 B1 | 11/2002 | Jayaraman ................. 623/1.15 |
| 6,488,700 B2 | 12/2002 | Klumb et al. ............... 623/1.12 |
| 6,488,701 B1 | 12/2002 | Nolting et al. .............. 623/1.13 |
| 6,506,211 B1 | 1/2003 | Skubitz et al. .............. 623/1.15 |
| 6,514,283 B2 | 2/2003 | DiMatteo et al. ............ 623/1.13 |
| 6,520,984 B1 | 2/2003 | Garrison et al. ............ 623/1.11 |
| 6,540,775 B1 | 4/2003 | Fischell et al. ............. 623/1.15 |
| 6,547,814 B2 | 4/2003 | Edwin et al. ............... 623/1.13 |
| 6,547,815 B2 | 4/2003 | Myers ........................ 623/1.13 |
| 6,558,414 B2 | 5/2003 | Layne ........................ 623/1.13 |
| 6,558,415 B2 | 5/2003 | Thompson .................. 623/1.16 |
| 6,569,193 B1 | 5/2003 | Cox et al. ................... 623/1.15 |
| 6,579,314 B1 | 6/2003 | Lombardi et al. .......... 623/1.44 |
| 6,613,081 B2 | 9/2003 | Kim et al. ................... 623/1.15 |
| 6,863,684 B2 | 3/2005 | Kim et al. ................... 623/1.15 |
| 6,878,162 B2 * | 4/2005 | Bales et al. ................. 623/1.15 |
| 7,001,419 B2 | 2/2006 | DiCaprio et al. ........... 623/1.11 |
| 7,204,848 B1 * | 4/2007 | Brown et al. ............... 623/1.15 |
| 2001/0039446 A1 | 11/2001 | Edwin et al. ............... 623/1.13 |
| 2001/0044650 A1 | 11/2001 | Simso et al. ................ 623/1.16 |
| 2001/0049551 A1 | 12/2001 | Tseng et al. ................ 623/1.15 |
| 2002/0007212 A1 | 1/2002 | Brown et al. ............... 623/1.16 |
| 2002/0040237 A1 | 4/2002 | Lentz et al. ................. 623/1.13 |
| 2002/0055770 A1 | 5/2002 | Doran et al. ................ 623/1.15 |
| 2002/0091437 A1 | 7/2002 | Tseng et al. ................ 623/1.13 |
| 2004/0024444 A1 | 2/2004 | Moore ........................ 623/1.15 |
| 2004/0230293 A1 | 11/2004 | Yip et al. .................... 623/1.16 |

FOREIGN PATENT DOCUMENTS

| | | |
|---|---|---|
| EP | 0938879 | 2/1999 |
| WO | 95/26695 | 10/1995 |
| WO | 00/30563 | 6/2000 |
| WO | 02/22024 | 3/2002 |
| WO | 02/055120 | 7/2002 |

* cited by examiner

VARYING CIRCUMFERENTIAL SPANNED CONNECTORS IN A STENT

CROSS-REFERENCE TO RELATED APPLICATIONS

This Application is a Divisional Application of U.S. application Ser. No. 10/606,168, filed Jun. 25, 2003, now U.S. Pat. No. 7,131,993, the entire contents of which is hereby incorporated herein by reference in its entirety.

BACKGROUND OF THE INVENTION

The use of stents in bodily lumen is well known. A stent is typically delivered in an unexpanded state to a desired location in a bodily lumen via a stent delivery device such as a catheter. Once the stent is at the desired bodily location, it is either expanded with a balloon or other suitable device or allowed to expand by, for example, withdrawing a restraining sheath.

Because a stent often must be delivered through tortuous anatomy, it is desirable for the stent to be flexible. Increased flexibility in a stent, however, typically comes at the expense of scaffolding strength. Moreover, design features which may result in increased flexibility may also result in protruding edges which may damage vessels walls or catheter balloons during delivery of the stent through tortuous vasculature. A compromise must often be reached between flexibility and stent strength.

There remains a need for a stent which has a high degree of flexibility in the unexpanded state, yet is capable of providing adequate scaffolding strength when expanded. It is desirable for a stent to be conformable and flexible enough to be tracked to the target site within the artery and to accommodate curvature of the vessel once deployed. It is also desirable for the stent to cover enough vessel to provide adequate scaffolding, and for the stent to be strong enough in the axial direction to resist foreshortening. In the case of a balloon expandable stent, it is also desirable for the stent to be crimpable. Further, it is desirable for the stent to adequately retain a coating.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, the invention is directed to a stent having a plurality of serpentine circumferential bands, and a plurality of connector columns. Each connector column is located between two adjacent serpentine circumferential bands. Each serpentine circumferential band has a proximal end portion, a distal end portion, a plurality of proximal turns at the proximal end portion and a plurality of distal turns at said distal end portion. Each connector column includes a plurality of connector struts. Each connector strut is coupled at a first end to a serpentine circumferential band and coupled at a second end to another serpentine circumferential band.

Desirably, the number of proximal turns in a serpentine circumferential band is a multiple of 3, and the number of connector struts in a connector column is a multiple of 2. Further, the number of connector struts in a connector column is desirably less than the number of proximal turns in an adjacent serpentine circumferential band.

In another embodiment, the invention is directed to a stent having a plurality of serpentine circumferential bands and a plurality of connector columns, each connector column being located between two adjacent serpentine circumferential bands. Each serpentine circumferential band has a proximal end portion, a distal end portion, a plurality of proximal turns at said proximal end portion and a plurality of distal turns at said distal end portion. Each connector column includes a plurality of connector struts, including at least one first type of connector strut and at least one second type of connector strut. Each connector strut is coupled at a first end to a serpentine circumferential band and coupled at a second end to another serpentine circumferential band.

Desirably, the number of proximal turns in a serpentine circumferential band is a multiple of 3, and the number of connector struts in a connector column is a multiple of 2.

In another embodiment, the invention is directed to a stent having a plurality of serpentine circumferential bands and a plurality of connector columns, each connector column located between two adjacent serpentine circumferential bands. Each serpentine circumferential band has a proximal end portion, a distal end portion, a plurality of proximal turns at said proximal end portion and a plurality of distal turns at said distal end portion. Each connector column includes a plurality of connector struts, including at least one first type of connector strut, at least one second type of connector strut and at least one third type of connector strut. Each connector strut is coupled at a first end to a serpentine circumferential band and coupled at a second end to another serpentine circumferential band.

In yet another embodiment, the invention is directed to a stent having a proximal end and a distal end, comprising a plurality of serpentine circumferential bands and a plurality of connector columns. Each serpentine circumferential band includes a proximal end portion and a distal end portion. The proximal end portion has a plurality of first proximal turns and a plurality of second proximal turns. The first proximal turns extend farther toward the stent proximal end than the second proximal turns. The distal end portion has a plurality of first distal turns and a plurality of second distal turns, and the first distal turns extend farther toward the stent distal end than said second distal turns.

Each connector column is located between two adjacent serpentine circumferential bands. Each connector column comprises a plurality of connector struts, including at least one first type of connector strut and at least one second type of connector strut. Each connector strut is coupled at a first end to a serpentine circumferential band and coupled at a second end to another serpentine circumferential band.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described embodiments of the invention.

BRIEF DESCRIPTION OF THE SEVERAL VIEWS OF THE DRAWING(S)

A detailed description of the invention is hereafter described with specific reference being made to the drawings.

Figure 2:
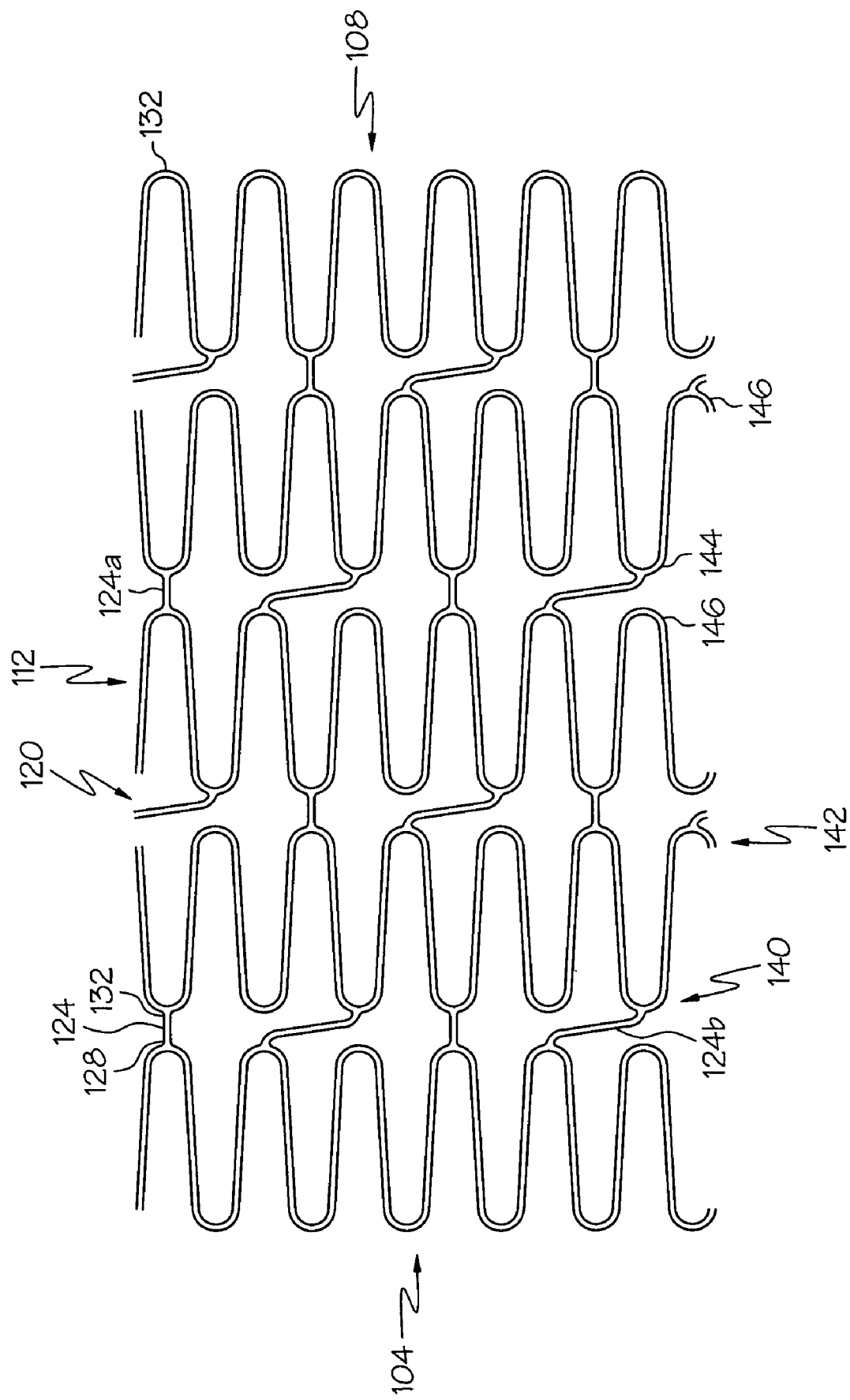
Figure 3:
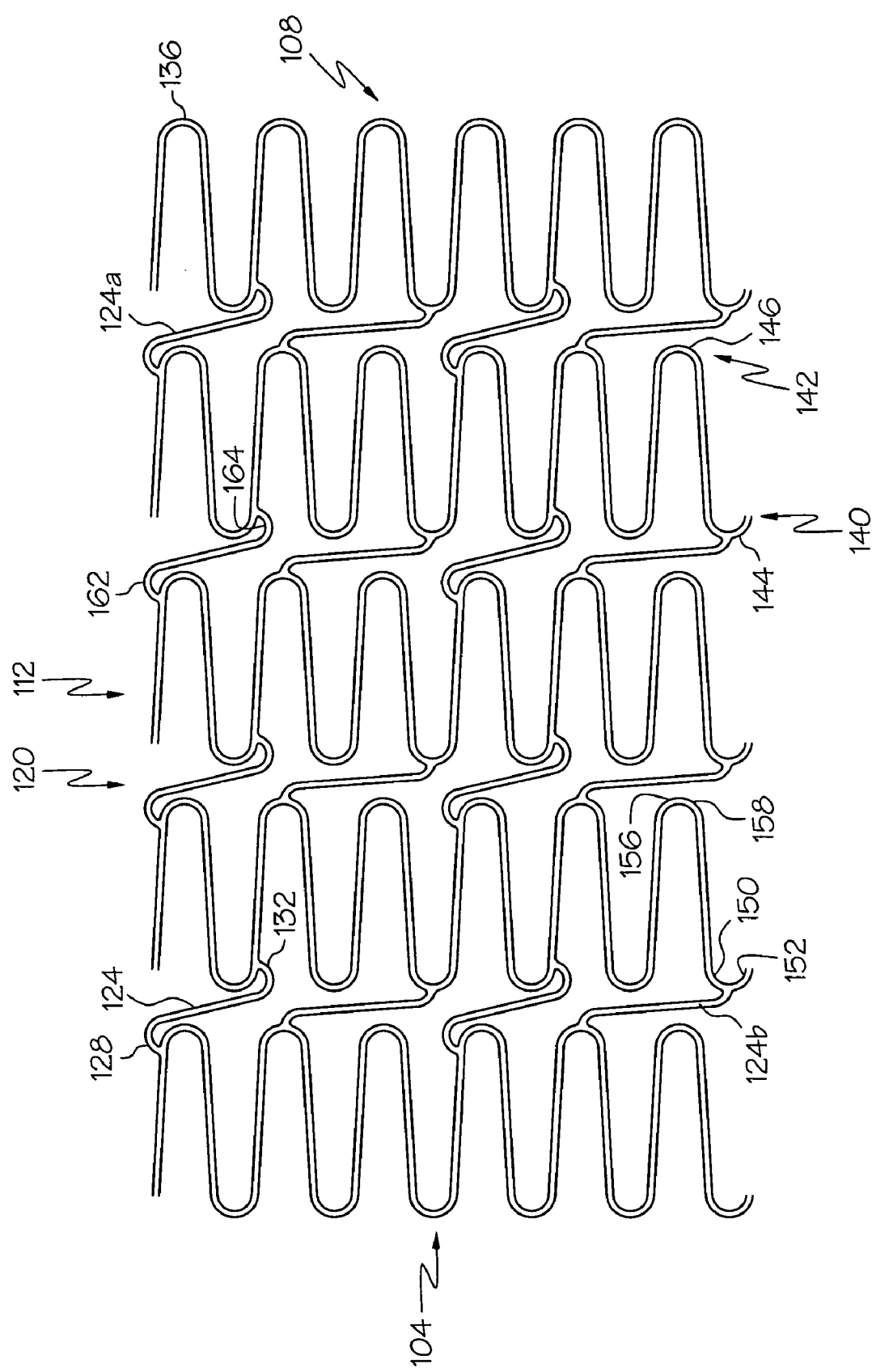
Figure 4:
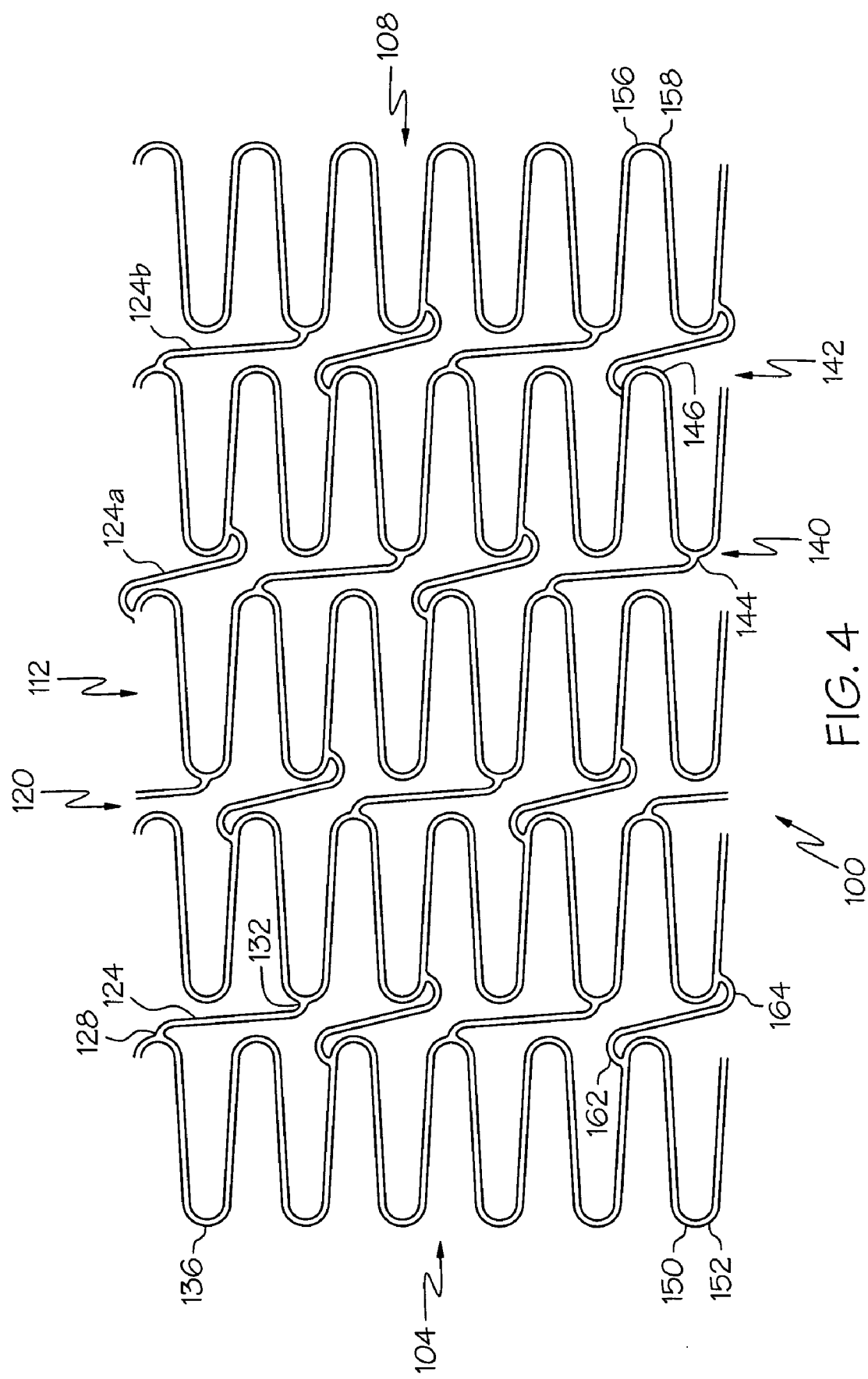
Figure 5:
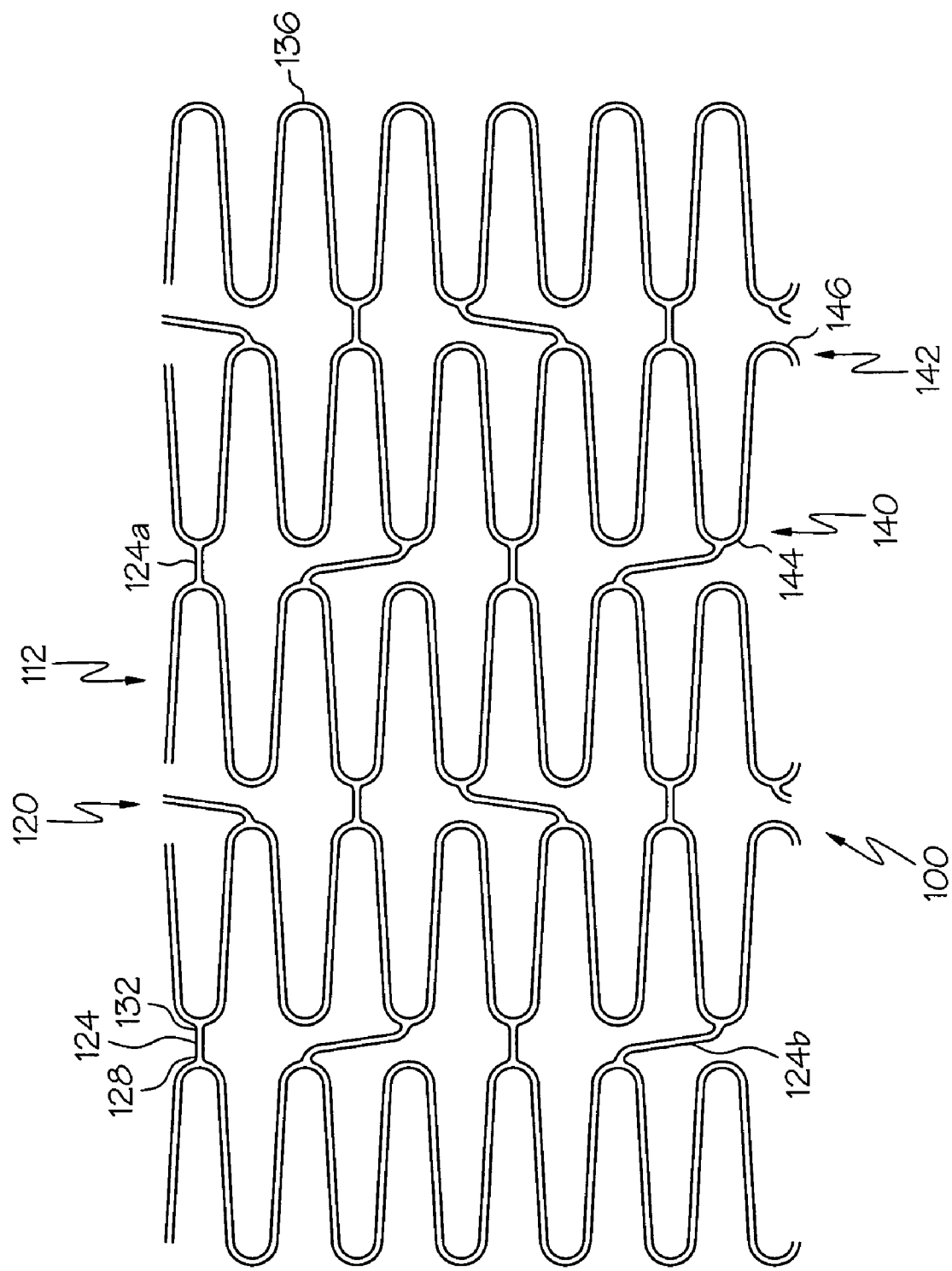
Figure 6:
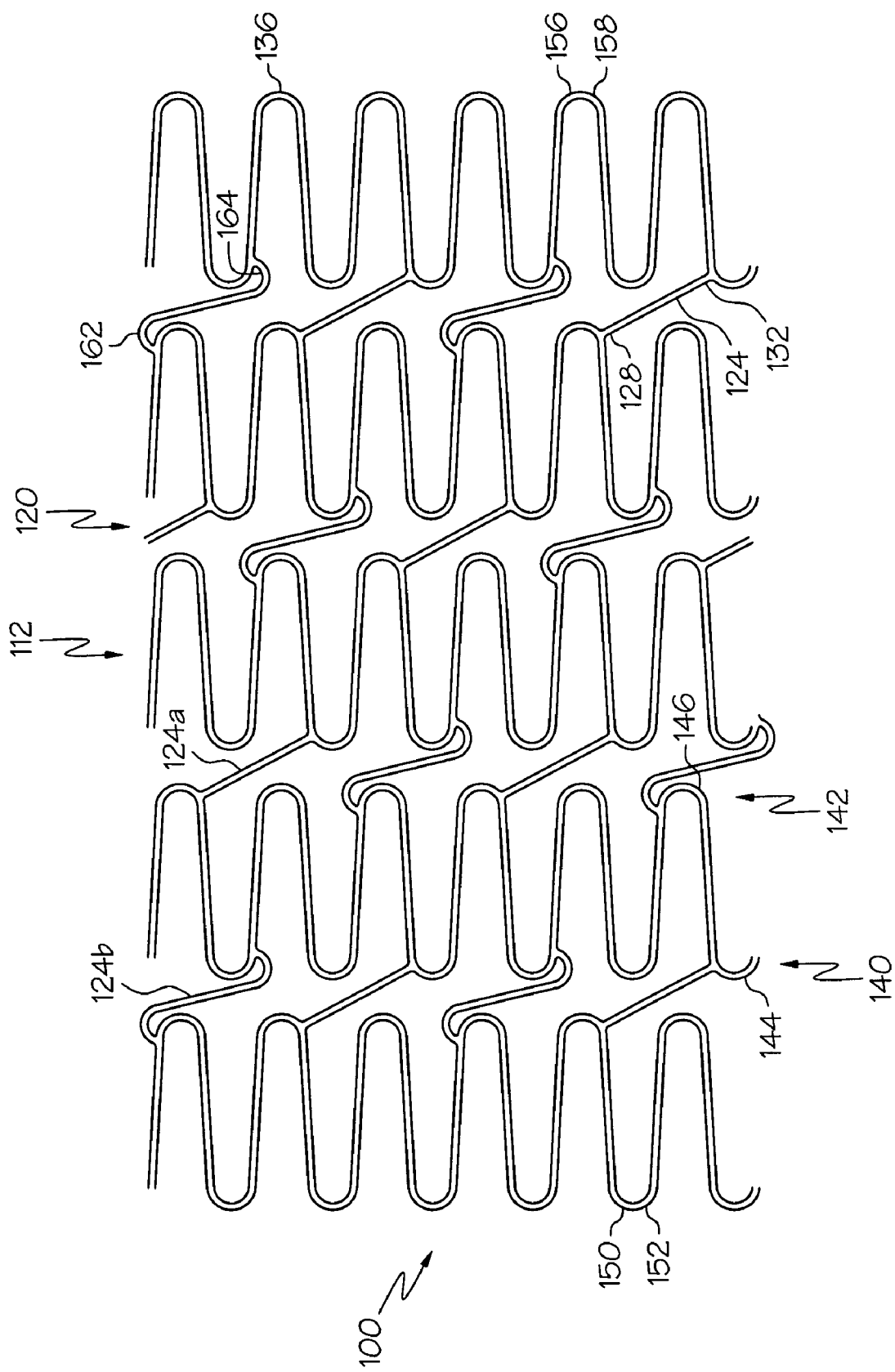
Figure 7:
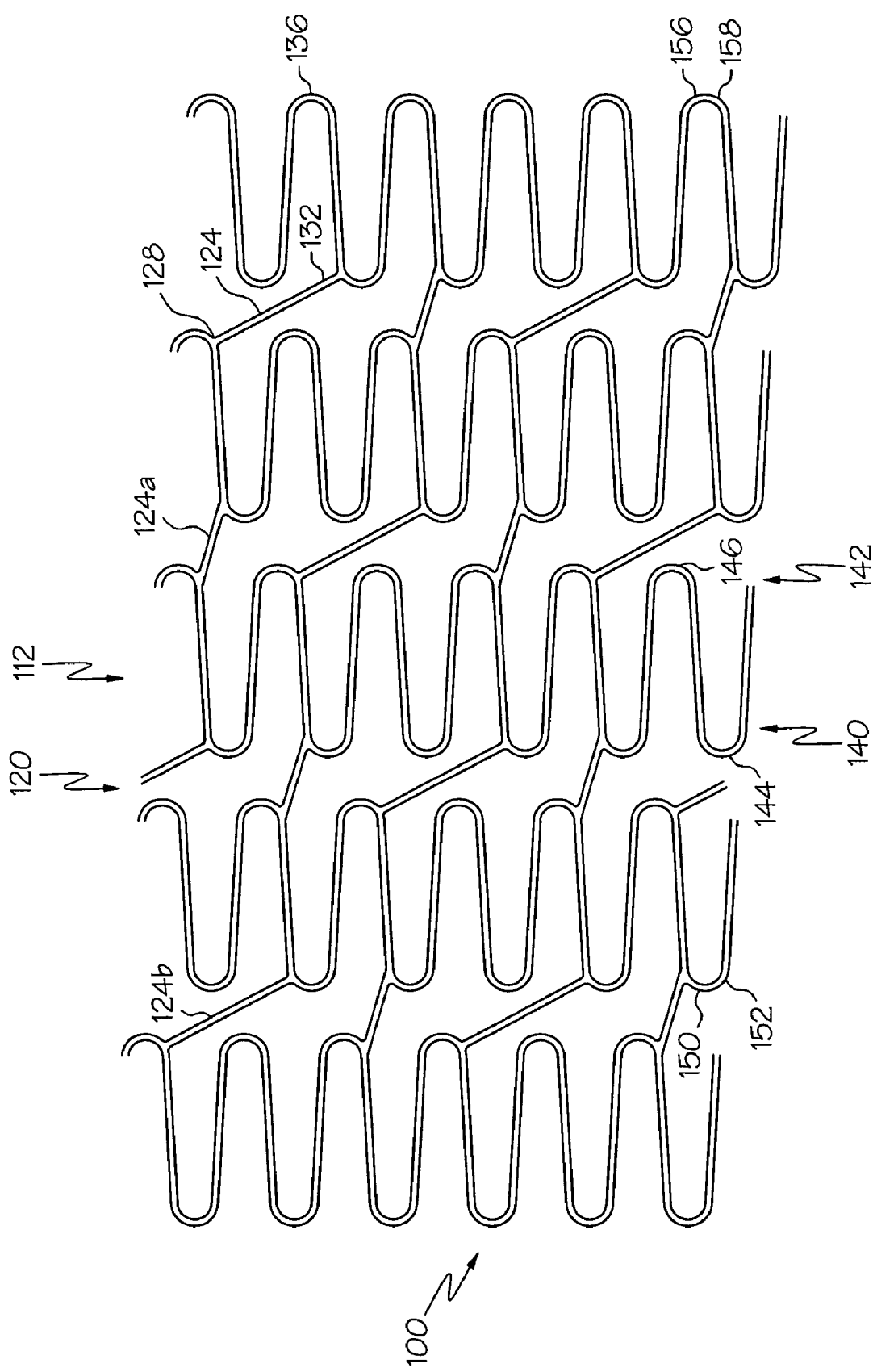
Figure 8:
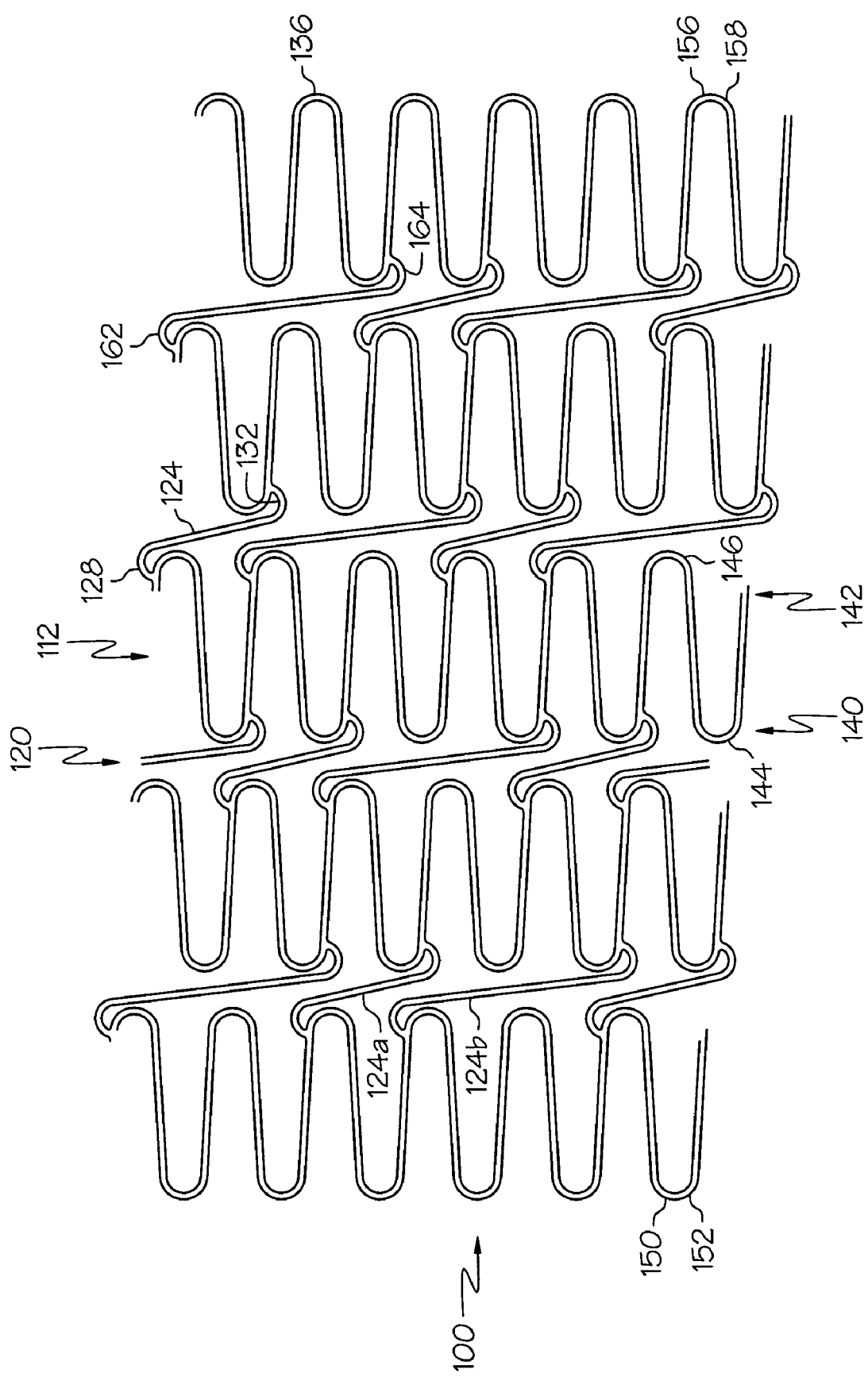
Figure 9:
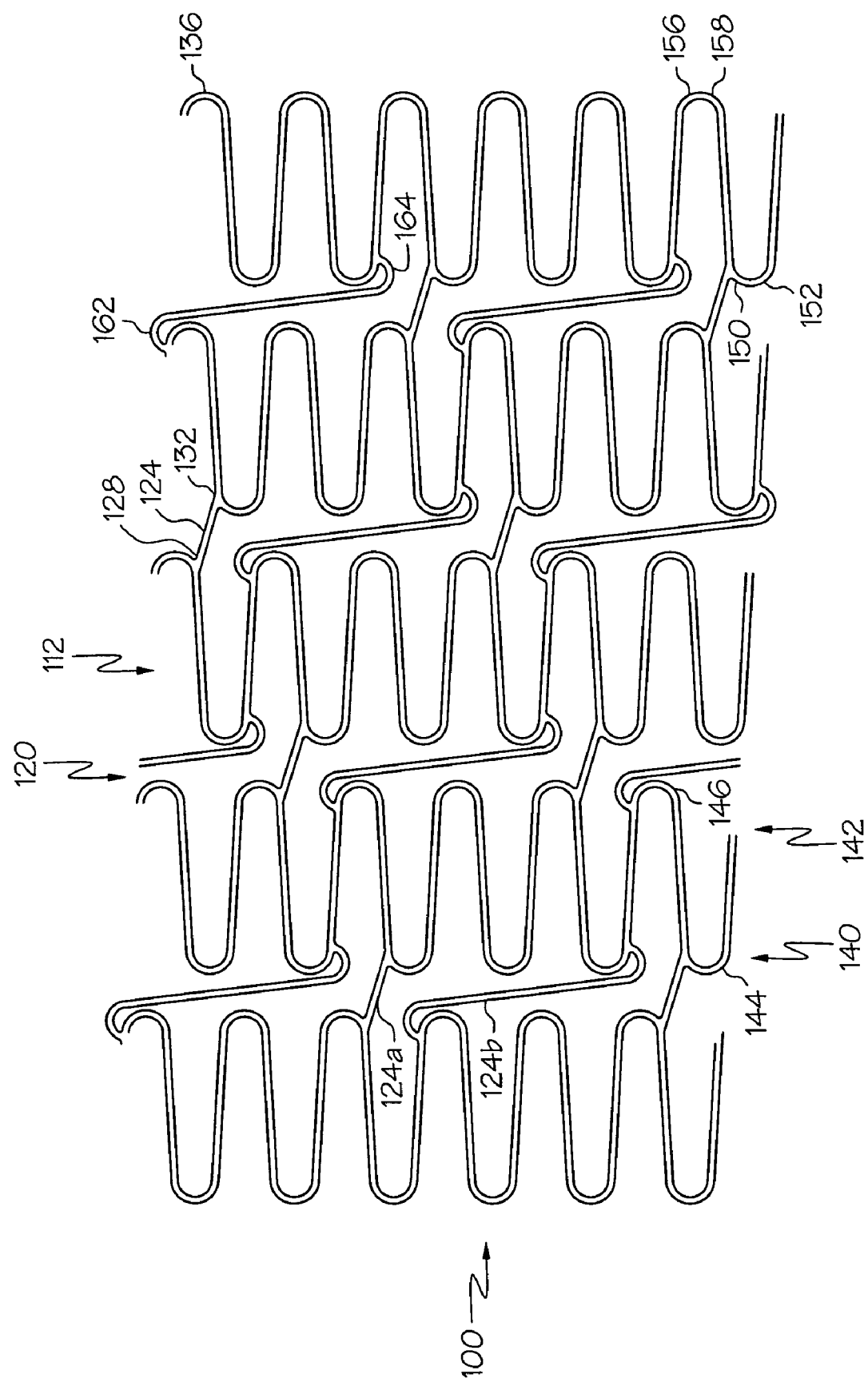
Figure 10:
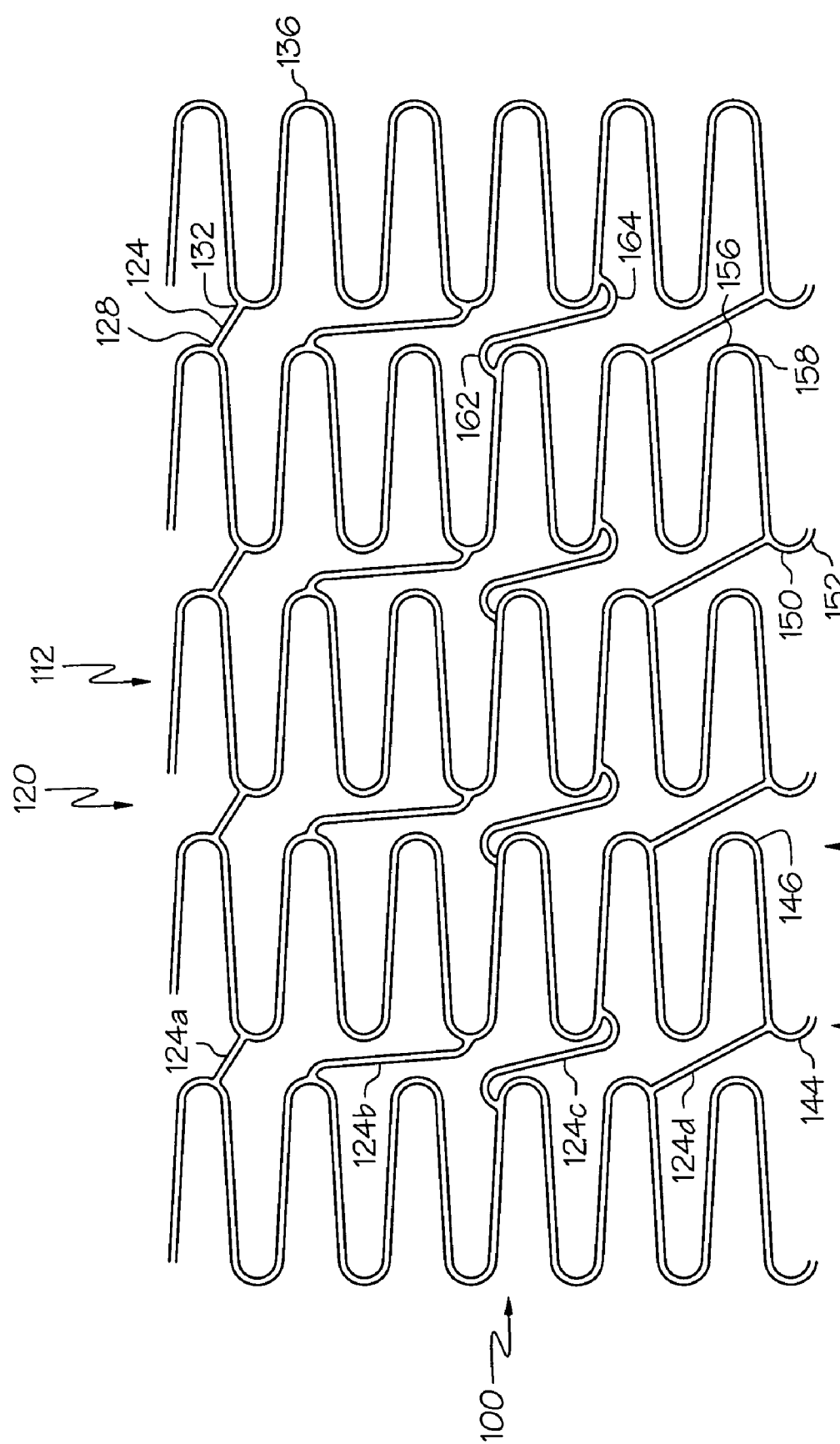
Figure 11:
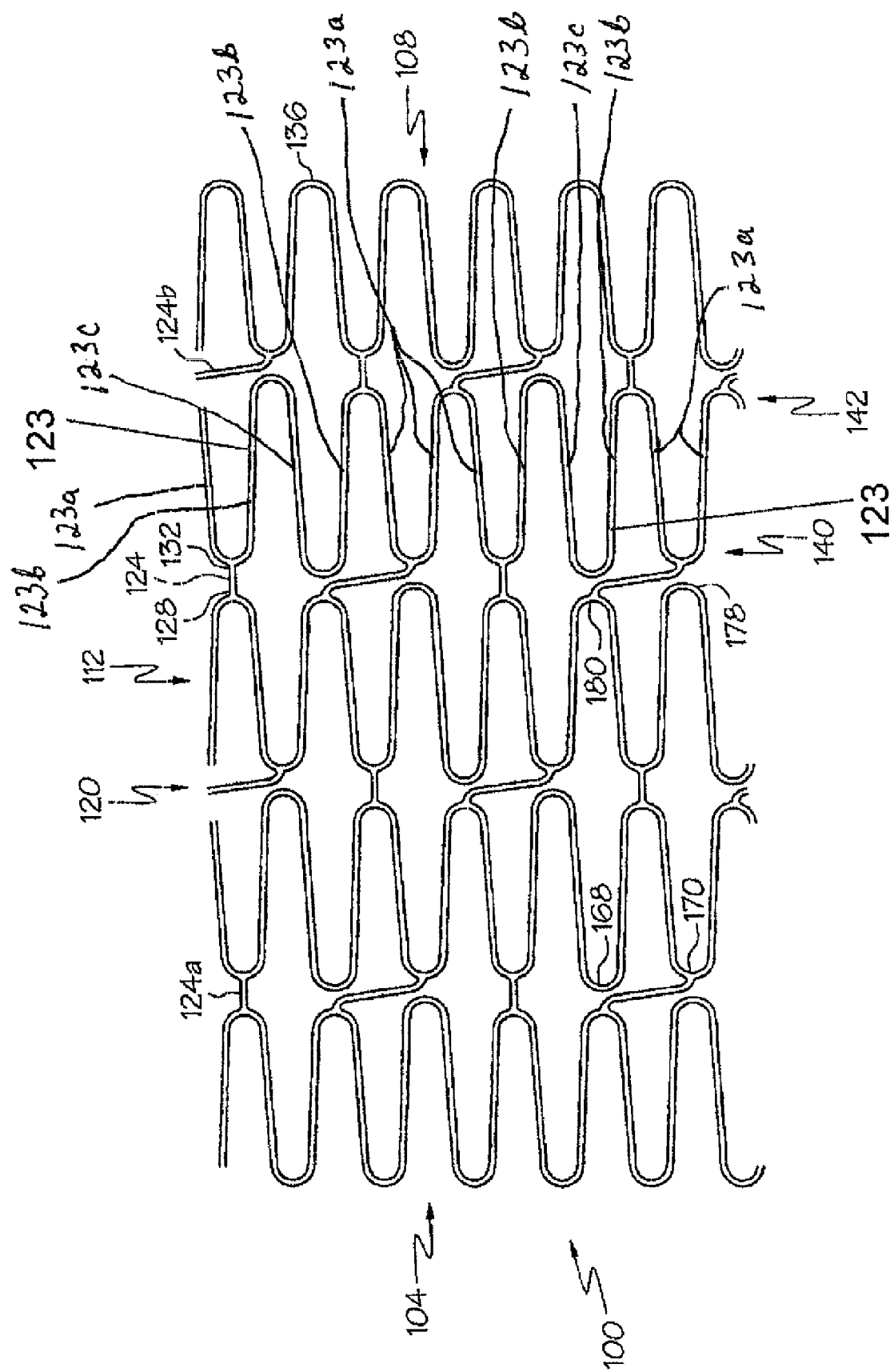
Figure 12:
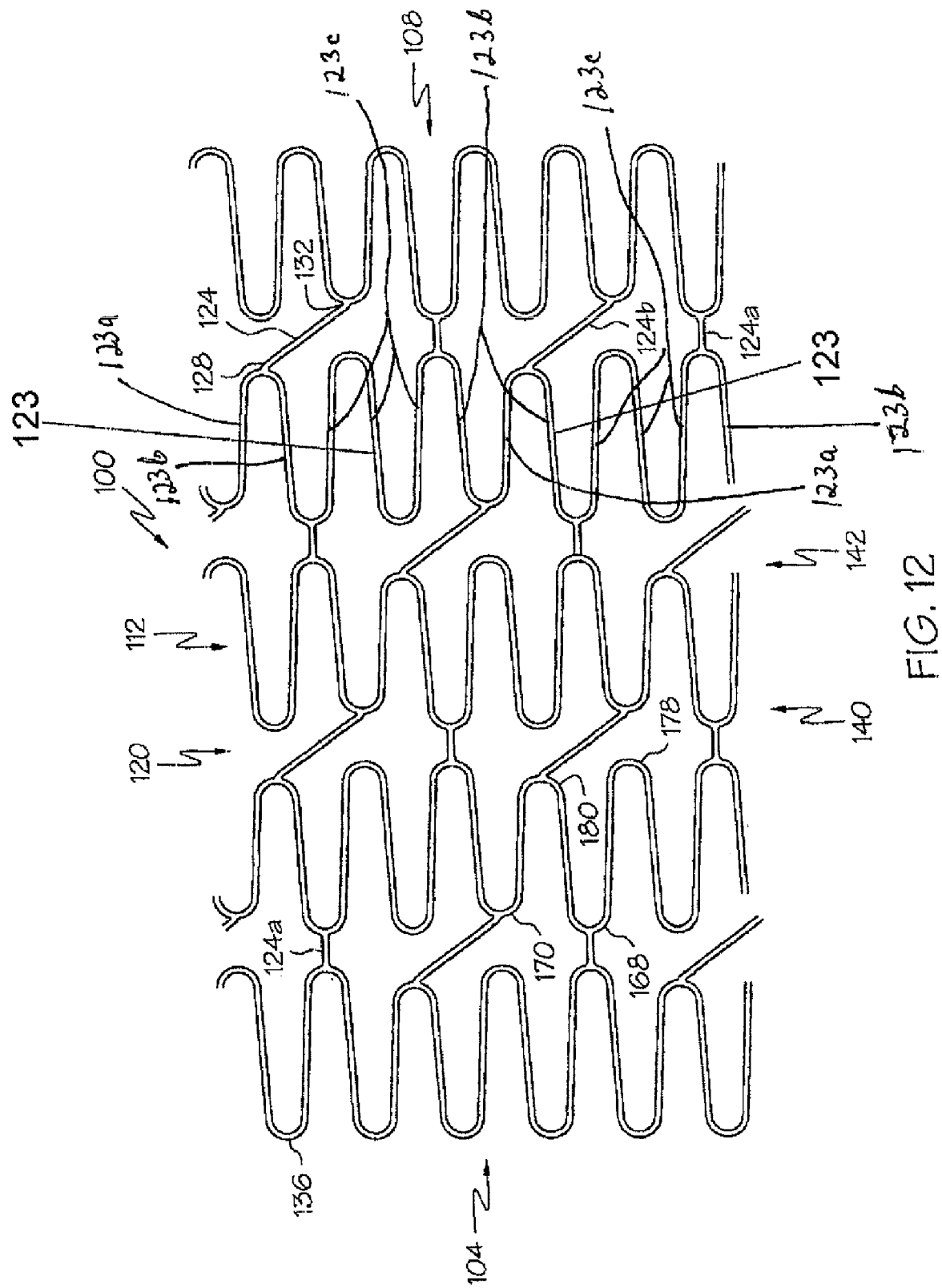
Figure 13:
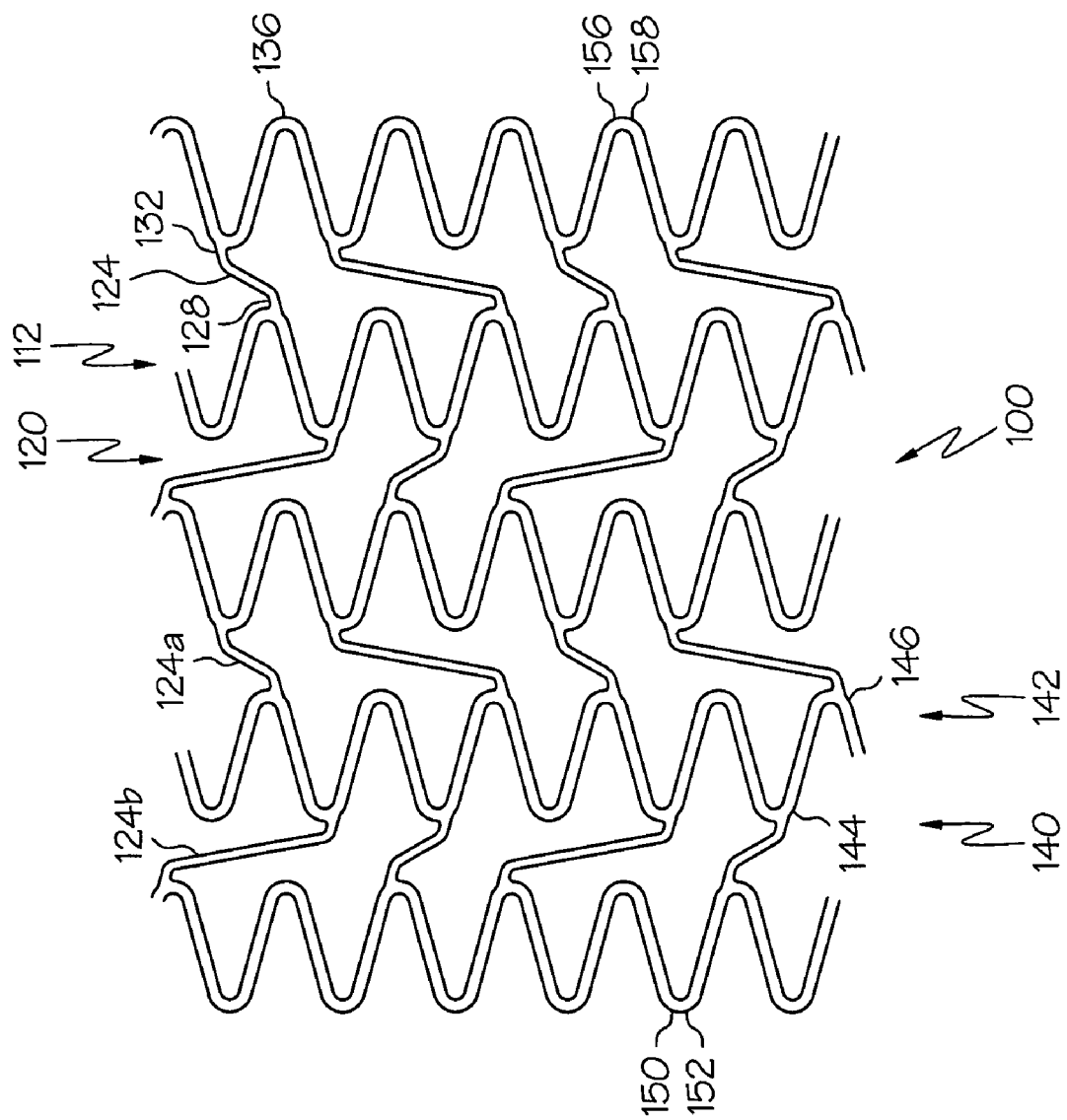
Figure 14:
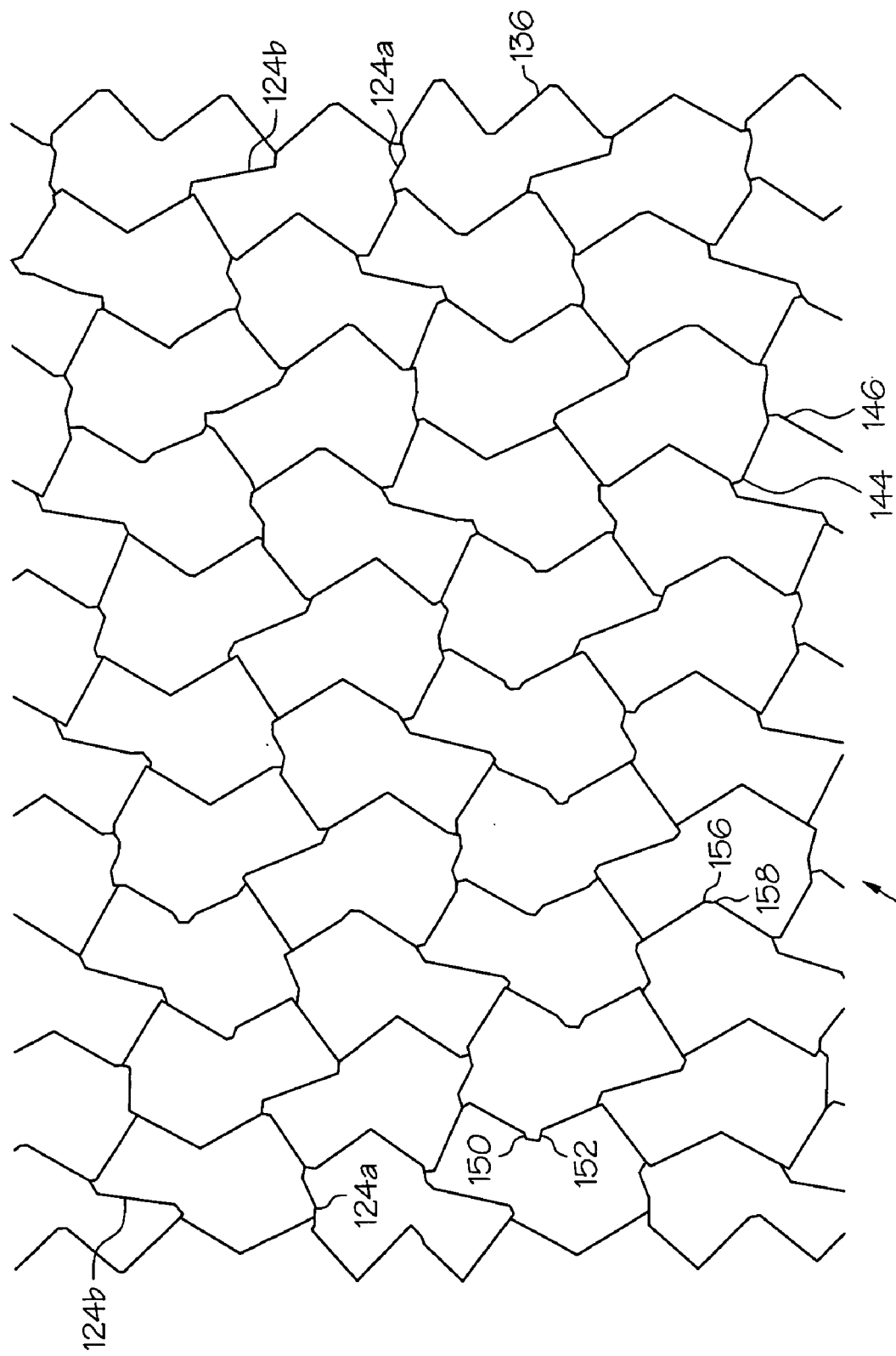
Figure 15:
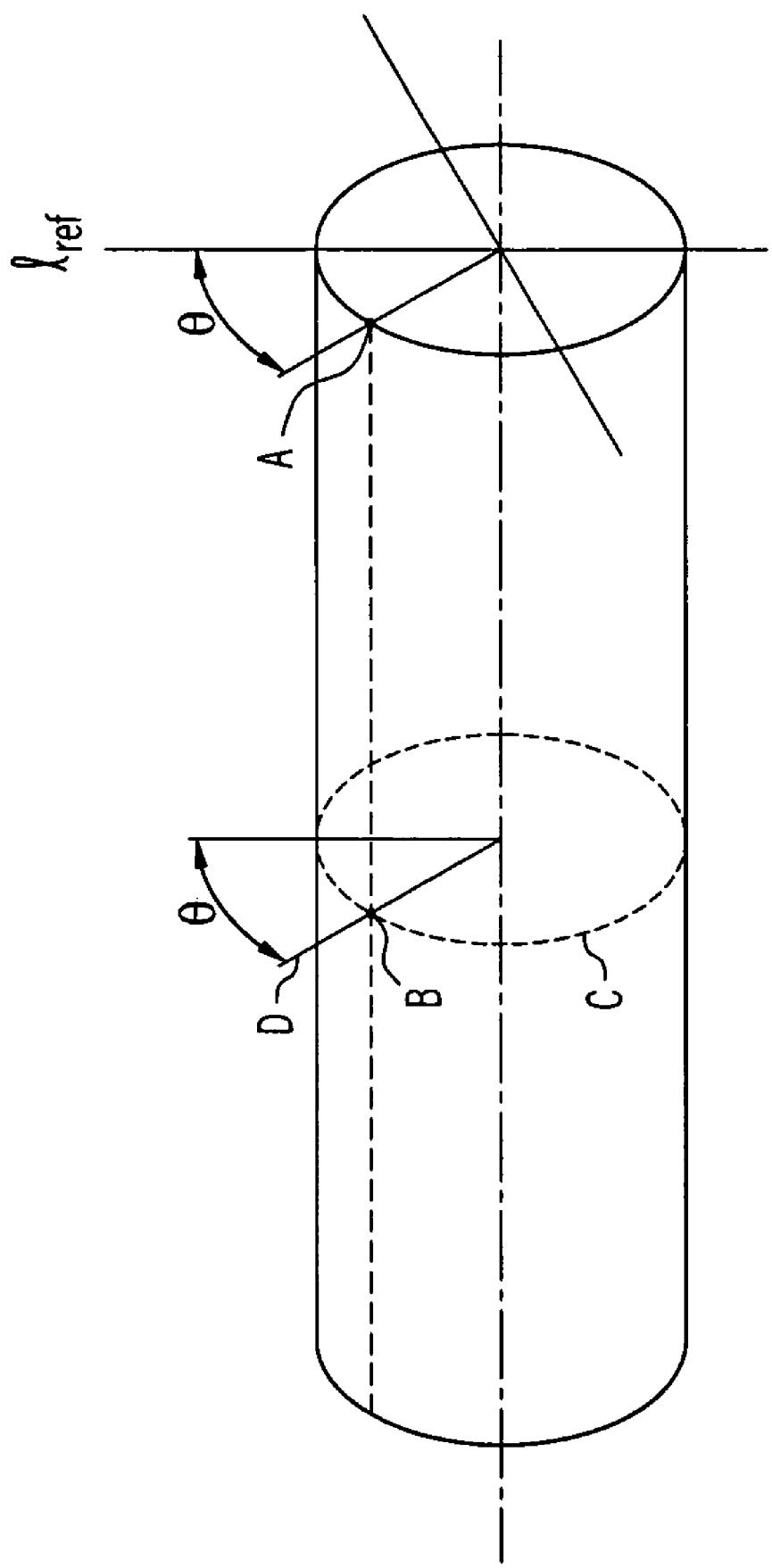

FIG. 1 shows an embodiment of an inventive stent.
FIG. 2 shows another embodiment of an inventive stent.
FIG. 3 shows another embodiment of an inventive stent.
FIG. 4 shows another embodiment of an inventive stent.
FIG. 5 shows another embodiment of an inventive stent.
FIG. 6 shows another embodiment of an inventive stent.
FIG. 7 shows another embodiment of an inventive stent.
FIG. 8 shows another embodiment of an inventive stent.
FIG. 9 shows another embodiment of an inventive stent.
FIG. 10 shows another embodiment of an inventive stent.
FIG. 11 shows another embodiment of an inventive stent.
FIG. 12 shows another embodiment of an inventive stent.
FIG. 13 shows another embodiment of an inventive stent.
FIG. 14 depicts a portion of an inventive stent in an expanded state.
FIG. 15 shows stent geometry and supplements various descriptions defined herein.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a stent such as that shown generally at 100 in FIG. 1, having a first free end 104 and a second free end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The similar turns 136 of adjacent serpentine circumferential bands 112 are desirably angularly aligned with one another, and more desirably longitudinally aligned with one another. Each serpentine circumferential band 112 may further be characterized as having a proximal end portion 140 and a distal end portion 142, a plurality of proximal turns 144 and a plurality of distal turns 146. Each turn 136 may further be described as a peak 114 or a trough 116, depending on whether it is at a distal or proximal end of the band.

For the purposes of this disclosure, the term 'angular alignment' is intended to describe a collection of points that are located at the same radial angle relative to a local reference axis of the stent. In other words, points that are angularly aligned will all reside in an area bounded on one side by the central longitudinal axis of the stent and extending in a common radial direction.

Referring to FIG. 15, point A is located at radial angle θ from a local reference axis $1_{ref}$. Point B is similarly located at radial angle θ from its local reference axis. Thus, points A and B are angularly aligned. Further, point D is located at radial angle θ from the same local reference axis point B. Thus, points A, B and D are all angularly aligned.

The term 'longitudinal alignment' is intended to describe a collection of points that are located at the same radial angle relative to a local reference axis of the stent that also form a line parallel to the central longitudinal axis of the stent. Referring to FIG. 15, points A and B are longitudinally aligned, while points A and D are not longitudinally aligned.

The term 'circumferential alignment' is intended to describe a collection of points that are equidistant from a first end of the stent and located about a circumference of the stent. In other words, points that are circumferentially aligned will all reside in a plane that is transverse to the longitudinal axis of the stent. Referring to FIG. 15, all points located on reference circumference C, including point B, are in circumferential alignment. It should be understood that to the extent that a stent as defined herein does not expand uniformly, points may still be circumferentially aligned even though they may not be located a uniform radial distance from the central longitudinal axis of the stent. When elements are described as being 'circumferentially offset,' it is intended to mean that the elements are not circumferentially aligned.

Further, when elements of the invention, such as serpentine circumferential band turns 136 or connector struts 124, are described as being angularly, longitudinally or circumferentially aligned or offset with respect to one another, it is typically intended to mean that the midpoints of said elements are in the described relationship.

Again referring to FIG. 1, desirably the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 1, the ratio of proximal turns 144 to connector struts 124 is 3:2.

Typically, each connector strut 124 will be substantially straight. The term 'substantially straight' is intended to encompass connector struts have curved end sections as shown for example at 124b. Each connector strut may be inclined at an angle of inclination relative to the longitudinal axis of the stent.

Desirably, each connector column 120 includes a first type of connector strut 124a and a second type of connector strut 124b. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Desirably, the first type of connector struts 124a in adjacent connector columns 120 are angularly aligned with one another, and more desirably longitudinally aligned with one another. Likewise, the second type of connector struts 124b in adjacent connector columns 120 are desirably angularly aligned with one another, and more desirably longitudinally aligned with one another.

Another embodiment of the invention is directed to a stent 100 as depicted in FIG. 2, having a first free end 104 and a second free end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Each serpentine circumferential band 112 may further be characterized as having a proximal end portion 140 and a distal end portion 142, a plurality of proximal turns 144 and a plurality of distal turns 146. Desirably, adjacent serpentine circumferential bands 112 reverse orientation with respect to one another. Thus, the proximal turns 144 of one serpentine circumferential band 112 are angularly and desirably longitudinally aligned with the distal turns 146 of the directly adjacent serpentine circumferential bands 112.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 2, the ratio of proximal turns 144 to connector struts 124 is 3:2.

Typically, each connector strut 124 will be substantially straight. The term 'substantially straight' is intended to include within its scope the connectors shown at 124b in FIG. 2 which are straight over most of their length but curve to connect to the serpentine circumferential band. Each connector strut may be inclined at an angle of inclination relative to the longitudinal axis of the stent, although some connector struts 124 of the present embodiment are parallel to the longitudinal axis.

Desirably, each connector column 120 includes a first type of connector strut 124a and a second type of connector strut 124b. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Desirably, the first type of connector struts 124a in adjacent connector columns 120 are longitudinally offset from one another. Further, the first type of connector struts 124a in one connector column 120 may be angularly or longitudinally aligned with the second type of connector struts 124b in the immediately adjacent connector columns 120.

Another embodiment of the invention is directed to a stent 100 as depicted in FIG. 3, having a first free end 104 and a second free end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Similar turns 136 of adjacent serpentine circumferential bands 112 are desirably angularly aligned with one another, and more desirably longitudinally aligned with one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 3, the ratio of proximal turns 144 to connector struts 124 is 3:2.

Desirably, each connector column 120 includes a first type of connector strut 124a and a second type of connector strut 124b. Each connector strut 124 may be inclined at an angle of inclination relative to the longitudinal axis of the stent 100. The first type of connector strut 124a may span a shorter circumferential distance than the second type of connector strut 124b. The first type of connector strut 124a may have an angle of inclination different than that of the second type of connector strut 124b. The second type of connector strut 124b may provide a greater axial strength than the first type of connector strut 124a. The second type of connector strut 124b may span a greater number of serpentine circumferential band turns 136 than the first type 124a.

Further, the first type of connector strut 124a may contain peaks 162 and troughs 164. The first type of connector strut 124a may connect to portions of adjacent band turns 136 that face away from one another. Thus, as depicted in FIG. 3, if the first end 128 of a first connector strut 124a is connected to a distal turn upper portion 156 of one serpentine circumferential band 112 and the connector strut 124a extends substantially in a downward direction, the second end 132 of the connector strut 124a will connect to a proximal turn lower portion 152 of the adjacent serpentine circumferential band 112.

Desirably, the first type of connector struts 124a in adjacent connector columns 120 are angularly aligned with one another, and more desirably longitudinally aligned with one another. Likewise, the second type of connector struts 124b in adjacent connector columns 120 are desirably angularly aligned with one another, and more desirably longitudinally aligned with one another.

Another embodiment of the invention is directed to a stent 100 as depicted in FIG. 4, having a first free end 104 and a second free end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Similar turns 136 of adjacent serpentine circumferential bands 112 are desirably angularly aligned with one another, and more desirably longitudinally aligned with one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 4, the ratio of proximal turns 144 to connector struts 124 is 3:2.

Desirably, each connector column 120 includes a first type of connector strut 124a and a second type of connector strut 124b. Each connector strut 124 may be inclined at an angle of inclination relative to the longitudinal axis of the stent 100. The first type of connector strut 124a may span a shorter circumferential distance than the second type of connector strut 124b. The first type of connector strut 124a may have an angle of inclination different than that of the second type of connector strut 124b. The second type of connector strut 124b may provide a greater axial strength than the first type of connector strut 124a. The second type of connector strut 124b may span a greater number of serpentine circumferential band turns 136 than the first type 124a.

Further, the first type of connector strut 124a may contain peaks 162 and troughs 164. The first type of connector strut 124a may connect to portions of adjacent band turns 136 that face away from one another. Thus, if the first end 128 of a first connector strut 124a is connected to a distal turn upper portion 156 of one serpentine circumferential band 112 and the connector strut 124a extends substantially in a downward direction, the second end 132 of the connector strut 124a will connect to a proximal turn lower portion 152 of the adjacent serpentine circumferential band 112.

Desirably, the first type of connector struts 124a in adjacent connector columns 120 are longitudinally offset from one another. Further, the first type of connector struts 124a in one connector column 120 may be longitudinally offset from the second type of connector struts 124b in the immediately adjacent connector columns 120.

A further embodiment of the invention is directed to a stent 100 as depicted in FIG. 5, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Each serpentine circumferential band 112 may further be characterized as having a proximal end portion 140 and a distal end portion 142, a plurality of proximal turns 144 and a plurality of distal turns 146. Desirably, adjacent serpentine circumferential bands 112 reverse orientation with respect to one another. Thus, the proximal turns 144 of one serpentine circumferential band 112 are angularly aligned and more desirably longitudinally aligned with the distal turns 146 of the directly adjacent serpentine circumferential bands 112.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 5, the ratio of proximal turns 144 to connector struts 124 is 3:2.

Typically, each connector strut 124 will be substantially straight. The term 'substantially straight' is intended to encompass the connectors shown in FIG. 5 including those shown at 124b having slight bends at the ends. Each connector strut may be inclined at an angle of inclination relative to the longitudinal axis of the stent, although some connector struts 124 of the present embodiment are parallel to the longitudinal axis.

Desirably, each connector column 120 includes a first type of connector strut 124a and a second type of connector strut 124b. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Desirably, the first type of connector struts 124a in adjacent connector columns 120 are longitudinally offset from one another. Further, the first type of connector struts 124a in one connector column 120 may be angularly or longitudinally aligned with the second type of connector struts 124b in the immediately adjacent connector columns 120.

Additionally, connector struts 124 in adjacent connector columns 120 may reverse orientation with respect to one another. For example, a second type of connector strut 124b in one connector column 120 may have a positive angle of inclination, and another second type of connector strut 124b in an adjacent connector column 120 may have a negative angle of inclination.

Another embodiment of the invention is directed to a stent 100 as depicted in FIG. 6, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The similar turns 136 of adjacent serpentine circumferential bands 112 are desirably angularly aligned with one another, and more desirably longitudinally aligned with one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 6, the ratio of proximal turns 144 to connector struts 124 is 3:2.

Desirably, each connector column 120 includes a first type of connector strut 124a and a second type of connector strut 124b. Each connector strut 124 may be inclined at an angle of inclination relative to the longitudinal axis of the stent 100. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may contain peaks 162 and troughs 164.

The first type of connector strut 124a may connect to portions of adjacent band turns 136 that face toward each other. Thus, if the first end 128 of a first connector strut 124a is connected to a distal turn lower portion 158 of one serpentine circumferential band 112 and the connector strut 124a extends substantially in a downward direction, the second end 132 of the first connector strut 124a will connect to a proximal turn upper portion 150 of another serpentine circumferential band 112.

The second type of connector strut 124b may connect to portions of adjacent band turns 136 that face away from one another. Thus, if the first end 128 of a second connector strut 124b is connected to a distal turn upper portion 156 of one serpentine circumferential band 112 and the connector strut 124b extends substantially in a downward direction, the second end 132 of the connector strut 124b will connect to a proximal turn lower portion 152 of the adjacent serpentine circumferential band 112.

Desirably, the first type of connector struts 124a and second type of connector struts 124b in adjacent connector columns 120 are longitudinally offset from one another.

Another embodiment of the invention is directed to a stent 100 as depicted in FIG. 7, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Similar turns 136 of adjacent serpentine circumferential bands 112 are desirably longitudinally offset from one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 7, the ratio of proximal turns 144 to connector struts 124 is 3:2.

Desirably, each connector column 120 includes a first type of connector strut 124a and a second type of connector strut 124b. Each connector strut 124 may be substantially straight, and may be inclined at an angle of inclination relative to the longitudinal axis of the stent 100. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

The first type of connector strut 124a may connect to portions of adjacent band turns 136 that face toward each other. Thus, if the first end 128 of a first connector strut 124a is connected to a distal turn lower portion 158 of one serpentine circumferential band 112 and the connector strut 124a extends substantially in a downward direction, the second end 132 of the first connector strut 124a will connect to a proximal turn upper portion 150 of another serpentine circumferential band 112.

The second type of connector strut 124b may connect to portions of adjacent band turns 136 that face toward each other. Thus, if the first end 128 of a second connector strut 124b is connected to a distal turn lower portion 158 of one serpentine circumferential band 112 and the connector strut 124b extends substantially in a downward direction, the second end 132 of the second connector strut 124b will connect to a proximal turn upper portion 150 of another serpentine circumferential band 112.

Desirably, the first type of connector struts 124a and second type of connector struts 124b in adjacent connector columns 120 are longitudinally offset from one another.

A further embodiment of the invention is directed to a stent 100 as depicted in FIG. 8, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The turns 136 of adjacent serpentine circumferential bands 112 are desirably longitudinally offset from one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 8, the ratio of proximal turns 144 to connector struts 124 is 3:2.

Desirably, each connector column 120 includes a first type of connector strut 124a and a second type of connector strut 124b. Each connector strut 124 may have peaks 162 and troughs 164, and may be inclined at an angle of inclination relative to the longitudinal axis of the stent 100. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Further, the first type of connector strut 124a may contain peaks 162 and troughs 164. The first type of connector strut 124a may connect to portions of adjacent band turns 136 that face away from one another. Thus, if the first end 128 of a first connector strut 124a is connected to a distal turn upper portion 156 of one serpentine circumferential band 112 and the connector strut 124a extends substantially in a downward direction, the second end 132 of the connector strut 124a will connect to a proximal turn lower portion 152 of the adjacent serpentine circumferential band 112.

The second type of connector strut 124b may connect to portions of adjacent band turns 136 that face away from one another. Thus, if the first end 128 of a second connector strut 124b is connected to a distal turn upper portion 156 of one serpentine circumferential band 112 and the connector strut 124b extends substantially in a downward direction, the second end 132 of the connector strut 124b will connect to a proximal turn lower portion 152 of the adjacent serpentine circumferential band 112.

Desirably, the first type of connector struts 124a and second type of connector struts 124b in adjacent connector columns 120 are longitudinally offset from one another.

In the embodiment of FIG. 8, the peaks of a circumferential band are not longitudinally aligned with either the peaks or the troughs of the adjacent circumferential band. It is within the scope of the invention for the peaks on one circumferential band to be angularly or longitudinally aligned with troughs or peaks on the adjacent circumferential band.

A further embodiment of the invention is directed to a stent 100 as depicted in FIG. 9, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The similar turns 136 of adjacent serpentine circumferential bands 112 are desirably longitudinally offset from one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 9, the ratio of proximal turns 144 to connector struts 124 is 3:2.

Desirably, each connector column 120 includes a first type of connector strut 124a and a second type of connector strut 124b. Each connector strut 124 may be inclined at an angle of inclination relative to the longitudinal axis of the stent 106. The second type of connector strut 124b may have one or more peaks 162 and one or more troughs 164. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

The first type of connector strut 124a may connect to portions of adjacent band turns 136 that face toward each other. Thus, if the first end 128 of a first connector strut 124a is connected to a distal turn lower portion 158 of one serpentine circumferential band 112 and the connector strut 124a extends substantially in a downward direction, the second end 132 of the first connector strut 124a will connect to a proximal turn upper portion 150 of another serpentine circumferential band 112.

The second type of connector strut 124b may connect to portions of adjacent band turns 136 that face away from one another. Thus, if the first end 128 of a second connector strut 124b is connected to a distal turn upper portion 156 of one serpentine circumferential band 112 and the connector strut 124b extends substantially in a downward direction, the second end 132 of the connector strut 124b will connect to a proximal turn lower portion 152 of the adjacent serpentine circumferential band 112.

Desirably, the first type of connector struts 124a and second type of connector struts 124b in adjacent connector columns 120 are longitudinally offset from one another.

As with the embodiment of FIG. 8, the peaks of a circumferential band are not longitudinally aligned with either the peaks or the troughs of the adjacent circumferential band. It is within the scope of the invention for the peaks on one circumferential band to be angularly or longitudinally aligned with troughs or peaks on the adjacent circumferential band.

Another embodiment of the invention is directed to a stent 100 as depicted in FIG. 10, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The similar turns 136 of adjacent serpentine circumferential bands 112 are desirably angularly aligned with one another, and more desirably longitudinally aligned with one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 10, the ratio of proximal turns 144 to connector struts 124 is 3:2.

Desirably, each connector column 120 includes a first type of connector strut 124a and a second type of connector strut 124b. Each connector column 120 may further include a third type of connector strut 124c, and may also include a fourth type of connector strut 124d. Each connector strut 124 may be inclined at an angle of inclination relative to the longitudinal axis of the stent 100. Each type of connector strut 124 may have one or more peaks 162 and one or more troughs 164. Each type of connector strut 124 may have a different length than the other types of connector struts 124. Each type of connector strut 124 may span a different circumferential distance than the other types of connector struts 124. Each type of connector strut 124 may have a different angle of inclination than the other types of connector struts. Each type of connector strut 124 may provide a different amount of axial strength to the stent 100 than the other types of connector struts 124.

The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

The first type of connector strut 124a may connect to portions of adjacent band turns 136 that face toward each other. Thus, if the first end 128 of a first connector strut 124a is connected to a distal turn lower portion 158 of one serpentine circumferential band 112 and the connector strut 124a extends substantially in a downward direction, the second end 132 of the first connector strut 124a will connect to a proximal turn upper portion 150 of another serpentine circumferential band 112.

The third type of connector strut 124c may connect to portions of adjacent band turns 136 that face away from one another. Thus, if the first end 128 of a third connector strut 124c is connected to a distal turn upper portion 156 of one serpentine circumferential band 112 and the connector strut 124c extends substantially in a downward direction, the second end 132 of the connector strut 124c will connect to a proximal turn lower portion 152 of the adjacent serpentine circumferential band 112. The third type of connector strut 124c may contain peaks 162 and troughs 164.

The fourth type of connector strut 124d may connect to portions of adjacent band turns 136 that face toward each other. Thus, if the first end 128 of a fourth connector strut 124d is connected to a distal turn lower portion 158 of one serpentine circumferential band 112 and the connector strut 124d extends substantially in a downward direction, the second end 132 of the fourth connector strut 124d will connect to a proximal turn upper portion 150 of another serpentine circumferential band 112.

Desirably, different types of connector struts 124 in adjacent connector columns 120 are angularly aligned with one another, and more desirably longitudinally aligned with one another. However, different types of connector struts 124 in adjacent connector columns 120 may be angularly or longitudinally offset from one another without departing from the invention.

Another embodiment of the invention is directed to a stent 100 as depicted in FIG. 11, having a proximal end 104 and a distal end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Each serpentine circumferential band 112 may further be characterized as having a proximal end portion 140 and a distal end portion 142, a plurality of first proximal turns 168, a plurality of second proximal turns 170, a plurality of first distal turns 178 and a plurality of second distal turns 180. Desirably, the first proximal turns 168 extend farther toward the stent proximal end 104 than the second proximal turns 170. Similarly, the first distal turns 178 desirably extend farther towards the stent distal end 108 than the second distal turns 180.

Desirably, adjacent serpentine circumferential bands 112 reverse orientation with respect to one another. Thus, the turns 136 located at the proximal end portion 140 of one serpentine circumferential band 112 are angularly aligned, and more desirably longitudinally aligned with the turns 136 located at the distal end portion 142 of the directly adjacent serpentine circumferential bands 112.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of turns 136 located at the proximal end portion 140 or distal end portion 142 of a serpentine circumferential band 112. For example, in the embodiment depicted in FIG. 11, the ratio of turns 136 located at a proximal end portion 140 of a serpentine circumferential band 112 to connector struts 124 is 3:2.

Typically, each connector strut 124 will be substantially straight. Each connector strut may be inclined at an angle of inclination relative to the longitudinal axis of the stent, although some connector struts 124 of the present embodiment are parallel to the longitudinal axis.

Desirably, each connector column 120 includes a first type of connector strut 124a and a second type of connector strut 124b. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Desirably, the first type of connector struts 124a in adjacent connector columns 120 are longitudinally offset from one another. Further, the first type of connector struts 124a in one connector column 120 may be angularly or longitudinally aligned with the second type of connector struts 124b in the next adjacent connector columns 120.

Further, as shown in FIG. 11, serpentine circumferential band turns 136 that are connected to a connector strut 124 are desirably the "second" type of turns, namely second proximal turns 170 if located in a proximal end portion 140 of the serpentine circumferential band 112 or second distal turns 180 if located in a distal end portion 142 of the serpentine circumferential band 112. Desirably, serpentine circumferential band turns 136 that are not connected to connector struts 124 comprise the "first" type of turns, namely first proximal turns 168 if located in a proximal end portion 140 of the serpentine circumferential band 112 or first distal turns 178 if located in a distal end portion 142 of the serpentine circumferential band 112.

As shown in FIG. 11, the peaks of a circumferential band are longitudinally aligned with the troughs of the adjacent circumferential band. It is also within the scope of the invention for the peaks on one circumferential band to be angularly or longitudinally aligned with peaks on the adjacent circumferential band or to be unaligned with peaks and troughs of an adjacent circumferential band.

A further embodiment of the invention is directed to a stent 100 as depicted in FIG. 12, having a proximal end 104 and a distal end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. Each serpentine circumferential band 112 may further be characterized as having a proximal end portion 140 and a distal end portion 142, a plurality of first proximal turns 168, a plurality of second proximal turns 170, a plurality of first distal turns 178 and a plurality of second distal turns 180. Desirably, the first proximal turns 168 extend farther toward the stent proximal end 104 than the second proximal turns 170. Similarly, the first distal turns 178 desirably extend farther towards the stent distal end 108 than the second distal turns 180.

Desirably, adjacent serpentine circumferential bands 112 reverse orientation with respect to one another. Thus, the turns 136 located at the proximal end portion 140 of one serpentine circumferential band 112 are angularly aligned, or more desirably longitudinally aligned with the turns 136 located at the distal end portion 142 of the directly adjacent serpentine circumferential bands 112.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of turns 136 located at the proximal end portion 140 or distal end portion 142 of a serpentine circumferential band 112. For example, in the embodiment depicted in FIG. 12, the ratio of turns 136 located at a proximal end portion 140 of a serpentine circumferential band 112 to connector struts 124 is 3:2.

Typically, each connector strut 124 will be substantially straight. Each connector strut may be inclined at an angle of inclination relative to the longitudinal axis of the stent, although some connector struts 124 of the present embodiment are parallel to the longitudinal axis.

Desirably, each connector column 120 includes a first type of connector strut 124a and a second type of connector strut 124b. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Desirably, the first type of connector struts 124a in adjacent connector columns 120 are longitudinally offset from one another. Further, the first type of connector struts 124a in one connector column 120 may be angularly or longitudinally aligned with the second type of connector struts 124b in the next adjacent connector columns 120.

Further, as shown in FIG. 12, serpentine circumferential band turns 136 that are connected to a second type of connector strut 124b are desirably the "second" type of turns, namely second proximal turns 170 if located in a proximal end portion 140 of the serpentine circumferential band 112 or second distal turns 180 if located in a distal end portion 142 of the serpentine circumferential band 112. Desirably, serpentine circumferential band turns 136 that are not connected to connector struts 124, and serpentine circumferential band turns 136 that are connected to the first type of connector strut 124a comprise the "first" type of turns, namely first proximal turns 168 if located in a proximal end portion 140 of the serpentine circumferential band 112 or first distal turns 178 if located in a distal end portion 142 of the serpentine circumferential band 112.

As can be seen in FIG. 11, struts 123 of different lengths extend between alternating turns 136 in an interior serpentine circumferential band 112. In the embodiment shown in FIG. 11, there are first struts 123a having a first length, second struts 123b having a second length and third struts 123c having a third length. As can be seen, the second length is greater than the first length and the third length is greater than the second length. In this embodiment, the first 123a, second 123b and third 123c struts are arranged in a repeating pattern as the interior serpentine band is traversed. In FIG. 11, as can be seen, the pattern is a third strut 123c, then a second strut 123b, then three consecutive first struts 123a, then a second strut 123b. For the embodiment shown in FIG. 12, the shown pattern is a first strut 123a, then a second strut 123b, then three consecutive third struts 123c, then a second strut 123b.

A further embodiment of the invention is directed to a stent 100 as depicted in FIG. 13, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each serpentine circumferential band 112 includes a plurality of turns 136. The turns 136 of adjacent serpentine circumferential bands 112 are desirably slightly longitudinally offset from one another. Each serpentine circumferential band 112 may further be characterized as having a proximal end portion 140 and a distal end portion 142, a plurality of proximal turns 144 and a plurality of distal turns 146. Each proximal turn 144 includes a proximal turn upper portion 150 and a proximal turn lower portion 152. Each distal turn 146 includes a distal turn upper portion 156 and a distal turn lower portion 158.

Desirably, the number of turns 136 per serpentine circumferential band 112 is a multiple of six. This may be accomplished by having the number of proximal turns 144 of a serpentine circumferential band 112 be a multiple of three, and the number of distal turns 146 of a serpentine circumferential band 112 be a multiple of three.

Desirably, the number of connectors 124 per connector column 120 is a multiple of two. Further, the number of connectors 124 per connector column 120 is desirably less than the number of proximal turns 144 or distal turns 146 per serpentine circumferential band 112. For example, in the embodiment depicted in FIG. 13, the ratio of proximal turns 144 to connector struts 124 is 3:2.

Desirably, each connector column 120 includes a first type of connector strut 124a and a second type of connector strut 124b. Each connector strut 124 may be inclined at an angle of inclination relative to the longitudinal axis of the stent 100. The first type of connector strut 124a may have a shorter length than the second type of connector strut 124b. The first type of connector strut 124a may span a shorter circumferential distance than the second type of connector strut 124b. The first type of connector strut 124a may have an angle of inclination different than that of the second type of connector strut 124b. The first type of connector strut 124a may provide a greater axial strength than the second type of connector strut 124b. The second type of connector strut 124b may span a greater number of serpentine circumferential band turns 136 than the first type 124a.

Connector struts 124 in adjacent connector columns 120 may reverse orientation with respect to one another. For example, a first type of connector strut 124a in one connector column 120 may have a positive angle of inclination, and a first type of connector strut 124a in an adjacent connector column 120 may have a negative angle of inclination. Similarly, a second type of connector strut 124b in one connector column 120 may have a positive angle of inclination, and another second type of connector strut 124b in an adjacent connector column 120 may have a negative angle of inclination.

The first type of connector strut 124a may connect to portions of adjacent band turns 136 that face away from one another. Thus, if the first end 128 of a first connector strut 124a is connected to a distal turn upper portion 156 of one serpentine circumferential band 112 and the connector strut 124a extends substantially in a downward direction, the second end 132 of the connector strut 124a will connect to a proximal turn lower portion 152 of the adjacent serpentine circumferential band 112. Further, because connector struts 124 in adjacent connector columns 120 desirably reverse orientation, a first type of connector strut 124a in an adjacent connector column 120 that extends substantially in an upward direction may have a first end 128 connected to a distal turn lower portion 158 of one serpentine circumferential band 112, and a second end 132 connected to a proximal turn upper portion 150 of an adjacent serpentine circumferential band 112.

Similarly, the second type of connector strut 124b may connect to portions of adjacent band turns 136 that face away from one another. Thus, if the first end 128 of a second connector strut 124b is connected to a distal turn upper portion 156 of one serpentine circumferential band 112 and the connector strut 124b extends substantially in a downward direction, the second end 132 of the connector strut 124b will connect to a proximal turn lower portion 152 of the adjacent serpentine circumferential band 112. Further, because connector struts 124 in adjacent connector columns 120 desirably reverse orientation, a second type of connector strut 124b in an adjacent connector column 120 that extends substantially in an upward direction may have a first end 128 connected to a distal turn lower portion 158 of one serpentine circumferential band 112, and a second end 132 connected to a proximal turn upper portion 150 of another serpentine circumferential band 112.

Desirably, the first type of connector struts 124a and second type of connector struts 124b in adjacent connector columns 120 are longitudinally offset from one another.

FIG. 14 depicts a portion of a stent 100 according to the embodiment shown in FIG. 13 in an expanded state. As shown in FIG. 14, the stent comprises a plurality of cells, each of which is bound at a proximal and distal end by a portion of a circumferential band and on the sides by two different types of connectors.

The invention is also directed to a stent having a plurality of interconnected circumferential bands which define a plurality of cells, the cells being bound at a distal end by a distal wall and at a proximal end by a proximal wall. The proximal and distal walls of the cell are connected to one another and differ in length from one another although the total length of each of the circumferential bands is the same. Desirably, each cell has two connector struts that connect the proximal and distal walls of the cell and the connector struts are of different lengths.

The invention is also directed to a stent combining various features of the embodiments described herein. Any feature of any embodiment disclosed could be incorporated into an inventive stent as disclosed herein. For example, the stents disclosed herein may be modified by employing different types of connector struts between the circumferential bands. To that end, any of the connectors and connector configurations disclosed herein may be used in any of the disclosed embodiments. For example, a stent could include the serpentine band structure of the stent of FIG. 12, having first and second distal turns and first and second proximal turns, with connector struts used with other embodiments. A type of connector strut may connect to portions of adjacent band turns that face away from one another. A type of connector strut may connect to portions of adjacent band turns that face toward one another.

Various other embodiments may include struts 124 that connect to serpentine circumferential bands 112 at the midpoint of proximal turns 144 or distal turns 146, and more specifically, at the inflection point. Further embodiments may include connector struts 124 that connect to portions of adjacent band turns 136 that face toward each other. For example, such a connector strut may have a first end 128 connected to a distal turn lower portion 158 of one serpentine circumferential band 112, and a second end 132 connected to a proximal turn upper portion 150 of another serpentine circumferential band 112. Another similar connector strut may have a reversed orientation, having a first end 128 connected to a distal turn upper portion 156 of one serpentine circumferential band 112, extend in a substantially upward direction, and have a second end 132 connected to a proximal turn lower portion 152 of another serpentine circumferential band 112. Embodiments may also include connector struts 124 that connect to portions of adjacent band turns 136 that face away from one another. Embodiments may include connector struts 124 that connect to similar portions of serpentine circumferential band turns 136. Thus, a connector strut may have a first end 128 connected to a distal turn lower portion 158 of one serpentine circumferential band 112, and a second end 132 connected to a proximal turn lower portion 152 of another serpentine circumferential band 112. Similarly, a connector strut may have a first end 128 connected to a distal turn upper portion 156 of one serpentine circumferential band 112, and a second end 132 connected to a proximal turn upper portion 150 of another serpentine circumferential band 112.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the circumferential bands and/or connectors may increase or decrease along portions of the stent or along the entire length of the stent. The amplitude and wavelength of several successive circumferential bands may remain constant while the width and/or thickness of the successive circumferential bands decrease.

The inventive stents may also be provided with end effects by modifying the stent such that that one or both ends are more rigid or more flexible than the remainder of the stent. Any of the inventive stents disclosed herein may be modified to have proximal-most and/or distal-most circumferential bands of a greater total circumferential length than the remaining circumferential bands. Any of the inventive stents disclosed herein may also be modified to have proximal-most and/or distal-most circumferential bands of a lesser total circumferential length than the remaining circumferential bands. Moreover, any of the inventive stents disclosed herein may also be modified so that one of the ends has circumferential bands of a lesser total circumferential length than the circumferential band of the other end which in turn is longer or shorter than the total length of any of the remaining circumferential bands.

Each serpentine circumferential band may be characterized as having a plurality of sections, each section having a wavelength and an amplitude. The wavelength of a serpentine circumferential band 112 section may be characterized as the distance from like points on a given serpentine circumferential band 112 in a direction perpendicular to the longitudinal axis of the stent, such as the distance from a given proximal turn 144 to the next adjacent proximal turn 144 of the serpentine circumferential band 112. The amplitude of a serpentine circumferential band 112 section may be characterized as the distance between end portions of the serpentine circumferential band along the longitudinal axis of the stent, for example, the distance from the peak of a proximal end portion 140 to the peak of a distal end portion 142. In some embodiments, each serpentine circumferential band 112 will have a constant wavelength and amplitude. In other embodiments, wavelength and amplitude may vary within a given serpentine circumferential band 112.

An example of an embodiment having serpentine circumferential band sections with varying amplitude is depicted in FIG. 11. In this embodiment, band turns 136 that are connected to connector struts 124 extend a lesser distance toward the proximal end 104 or distal end 108 of the stent than band turns 136 that are not connected to connector struts 124. In the embodiment shown in FIG. 12, band turns 136 that are connected to the second type of connector struts 124b extend a lesser distance toward the proximal end 104 or distal end 108 of the stent than band turns 136 that are connected to the first type of connector struts 124a or not connected to connector struts 124. Various other embodiments may include serpentine circumferential bands 112 wherein band turns 136 that are connected to the first type of connector struts 124a extend a lesser distance toward the proximal end 104 or distal end 108 of the stent than band turns 136 that are connected to the second type of connector struts 124b or not connected to connector struts 124. With reference to FIGS. 11 and 12, varying amplitude of serpentine circumferential band 112 sections may be used in combination with different types of connector struts 124. It should be understood that all types of connector struts may extend from first distal turns 178 to first proximal turns 168 or to second proximal turns 170. Similarly, all types of connector struts may extend from second distal turns 180 to first proximal turns 168 or to second proximal turns 170.

Also, one or both of the end circumferential bands may be modified to be of a greater longitudinal extent than the remaining circumferential bands or to be of a lesser longitudinal extent than the remaining circumferential bands. Each of the two end circumferential bands may differ in longitudinal extent with one another and with the remaining circumferential bands.

The invention also contemplates modifying the ends of any of the inventive stents so that the two proximal-most and/or two distal-most circumferential bands have more connections therebetween than the remaining circumferential bands or fewer connections therebetween than the remaining circumferential bands.

Further, the proximal-most and/or distal-most circumferential bands may be of a greater mass than the remaining bands or a lower mass than the remaining bands. They may be thicker than the remaining bands or thinner than the remaining bands.

It is understood that the above discussed modifications resulting in end effects may be applied to multiple circumferential bands at one or both ends of the stent and are not limited to the proximal-most and distal-most circumferential bands.

The stents disclosed herein may also be modified by changing the number of connections between adjacent circumferential bands. Thus, where larger cells are desired, fewer connections between circumferential bands will be provided. Where smaller cells are desired, more connections between bands will be provided. Any of the embodiments shown may also be modified only at various desired portions of the stent. Thus, some sections of the stent may have more connections and other sections may have fewer connections. More flexibility may be achieved by providing fewer connections between adjacent circumferential bands.

The connectors may range in width from being wider than the width of the widest struts in the stent, to being narrower than the narrowest struts in the stent or anywhere in-between. Regions of different flexibility may also be achieved by using a wider connection in some regions. For example, wider connections may be used at one or both of the ends of the stent, and narrower connections in the other regions of the stent (e.g. the middle portions), or vice versa.

The invention also contemplates embodiments in which the spacing between adjacent circumferential bands varies in different portions of the stent. For example, the proximal-most circumferential band and/or the distal-most circumferential band may be spaced further apart from the circumferential bands adjacent thereto or may be spaced closer thereto. This would result in using longer connectors between the end bands or shorter connectors, depending on the configuration. In one embodiment, both the proximal-most and the distal-most circumferential bands are more closely spaced to adjacent circumferential bands than the spacing between the remaining circumferential bands and further, the spacing between the proximal-most circumferential band and the circumferential band adjacent thereto differs from the spacing between the distal-most circumferential band and the circumferential band adjacent thereto.

It is also within the scope of the invention for any of the stents disclosed herein to have connectors extending from regions other than peaks and trough or corners of peaks and troughs. For example, the connectors may extend from positions midway between adjacent peaks and troughs, from position one quarter of the way between peaks and troughs, from positions three quarters of the way between peaks and troughs or anywhere else between peaks and troughs.

As shown in the various embodiments, the connections between circumferential bands may extend in a longitudinal direction or may have first and second ends which are circumferentially and longitudinally offset from one another, as in the case of connections extending at an oblique angle. The connections may also include portions which are non-parallel to the longitudinal axis of the stent.

The 'phase relationship' between adjacent circumferential bands may also be modified in any of the embodiments. For example, in various embodiments of the invention, peaks of adjacent cylindrical bands may be in longitudinal alignment with one another, or may be unaligned with one another in the longitudinal direction. Similarly, peaks on one band may be longitudinally aligned with troughs on an adjacent circumferential band or may be unaligned with troughs on an adjacent circumferential band. Some of the adjacent circumferential bands may be aligned while other adjacent bands may not be aligned.

The stent patterns disclosed herein may also be used for bifurcated stents. One or more legs and/or the trunk of a bifurcated stent may be provided with any of the stent designs disclosed herein.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design. The stent may also be manufactured by welding individual sections, for example, circumferential bands, together. Any other suitable stent manufacturing process may also be used.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys.

The invention also contemplates the use of more than one material in the inventive stents. For example, the first undulating bands and the second undulating bands may be made of different materials. Optionally, the connectors may be made of a different material than the first and/or second undulating bands.

The inventive stents may be provided in mechanically expandable form, in self-expanding form or as a hybrid of the two. Mechanically expandable stents, in accordance with the invention, may be expanded using any suitable mechanical device including a balloon.

The inventive stents may include suitable radiopaque coatings or markers. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time. The increased surface area of a stent having bent struts provides for increased drug coatability. The bent struts also provide for point contact with a crimper versus strut/strut contact. Less contact with the crimper results in less disruption of the drug coating.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor, cell cycle inhibitors including CD inhibitors, thymidine kinase ("TK") and other agents useful for interfering with cell proliferation the family of bone morphogenic proteins ("BMP"s"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP"s are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA"s encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The inventive stents may find use in coronary arteries, renal arteries, peripheral arteries including iliac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus, the prostate and the bowels.

Suitable stent delivery devices such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in U.S. provisional application 60/238,178.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 3, or on claim 1, claim 5 may be taken as alternatively dependent on claim 4, claim 3, or on claim 1; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent having a proximal end, a distal end and a longitudinal axis, the stent comprising:
    a plurality of serpentine bands including a first end serpentine band, a second end serpentine band and at least one interior serpentine band, said at least one interior serpentine band comprising alternating turns connected by struts, the struts comprising a plurality of first struts having a first length, a plurality of second struts having a second length and a plurality of third struts having a third length, the second length greater than the first length, the third length greater than the second length, the first, second and third struts arranged in a predetermined pattern as said at least one interior serpentine band is traversed, said predetermined pattern repeating as said at least one interior serpentine band is traversed in its entirety, wherein the predetermined pattern is a first strut, then a second strut, then three consecutive third struts, then a second strut or the predetermined pattern is a third strut, then a second strut, then three consecutive first struts, then a second strut; and
    a plurality of connector columns, each connector column located between two adjacent serpentine bands, each connector column comprising a plurality of connector struts including at least one first connector strut and at least one second connector strut, each connector strut coupled at a first end to a serpentine band and coupled at a second end to another serpentine band;
    wherein a first connector strut is parallel to the longitudinal axis, and the first end of a second connector strut is longitudinally and circumferentially offset from the second end of the second connector strut.

2. The stent of claim 1, the at least one interior serpentine band including a first interior serpentine band and second interior serpentine band, the bands each having a proximal end portion comprising a plurality of proximal turns and a distal end portion comprising a plurality of distal turns;
    the proximal turns of each of the first and second interior serpentine bands consisting of first proximal turns and second proximal turns, wherein said first proximal turns extend farther toward the stent proximal end than said second proximal turns, said first proximal turns aligned with one another around the circumference of the stent, and said second proximal turns aligned with one another around the circumference of the stent; and
    said first and second interior serpentine bands each comprising first distal turns and second distal turns, wherein said first distal turns extend farther toward the stent distal end than said second distal turns.

3. The stent of claim 2 the first connector strut being shorter than the second connector strut.

4. The stent of claim 2, wherein said first connector strut is coupled at the first end to a first distal turn of an interior serpentine band and coupled at the second end to a first proximal turn of another interior serpentine band.

5. The stent as recited in claim 2, wherein said second connector strut is coupled at the first end to a second distal turn of an interior serpentine band, and coupled at the second end to a second proximal turn of another interior serpentine band.

6. The stent as recited in claim 5, wherein distal turns of an interior serpentine band that are not connected to a connector strut comprise first distal turns.

7. The stent as recited in claim 5, wherein the first connector struts of a connector column are circumferentially offset from the first connector struts of an adjacent connector column.

8. The stent as recited in claim 2, wherein the proximal turns of an interior serpentine band are aligned with the distal turns of an adjacent interior serpentine band in a stent longitudinal direction.

9. The stent as recited in claim 8, wherein proximal turns of an interior serpentine band that are not connected to a connector strut comprise first proximal turns.

10. The stent as recited in claim 2, wherein the number of proximal turns in an interior serpentine band is a multiple of 3, and wherein the number of connector struts in a connector column is a multiple of 2, and wherein the number of connector struts in a connector column is less than the number of proximal turns in an adjacent interior serpentine band.

11. The stent as recited in claim 2, wherein proximal turns of a serpentine band that are not connected to a connector strut comprise first proximal turns.

12. The stent as recited in claim 11, wherein distal turns of a serpentine band that are not connected to a connector strut comprise first distal turns.

13. The stent as recited in claim 2, wherein the proximal turns of a serpentine band are aligned with the distal turns of an adjacent serpentine band in a stent longitudinal direction.

14. The stent as recited in claim 13, wherein a first proximal turn of a serpentine band is aligned with a second distal turn of an adjacent serpentine band in a stent longitudinal direction.

15. The stent as recited in claim 1, wherein the second connector strut spans a greater circumferential distance than the first connector strut.

* * * * *